(12) United States Patent
Emami et al.

(10) Patent No.: US 9,999,756 B2
(45) Date of Patent: Jun. 19, 2018

(54) SYSTEM FOR DELIVERY OF GASEOUS IMAGING CONTRAST AGENTS AND METHODS FOR USING SAME

(71) Applicant: The Trustees of the University of Pennsylvania, Philadelphia, PA (US)

(72) Inventors: Kiarash Emami, Abington, PA (US); Stephen J. Kadlecek, Philadelphia, PA (US); Rahim R. Rizi, Ambler, PA (US); Masaru Ishii, Bel Air, MD (US); Hooman Hamedani, Philadelphia, PA (US)

(73) Assignee: THE TRUSTEES OF THE UNIVERSITY OF PENNSYLVANIA, Philadelphia, PA (US)

( * ) Notice: Subject to any disclaimer, the term of this patent is extended or adjusted under 35 U.S.C. 154(b) by 642 days.

(21) Appl. No.: 14/527,369

(22) Filed: Oct. 29, 2014

(65) Prior Publication Data

US 2016/0038727 A1    Feb. 11, 2016

Related U.S. Application Data

(63) Continuation of application No. PCT/US2013/039531, filed on May 3, 2013.
(Continued)

(51) Int. Cl.
| | | |
|---|---|---|
| A61B 5/05 | (2006.01) |
| A61M 31/00 | (2006.01) |
| A61B 5/055 | (2006.01) |
| A61B 5/08 | (2006.01) |
| A61M 16/12 | (2006.01) |

(Continued)

(52) U.S. Cl.
CPC ........... *A61M 31/005* (2013.01); *A61B 5/055* (2013.01); *A61B 5/0813* (2013.01); *A61K 49/08* (2013.01); *A61M 16/0488* (2013.01); *A61M 16/06* (2013.01); *A61M 16/0875* (2013.01); *A61M 16/12* (2013.01); *A61M 16/122* (2014.02); *A61M 16/202* (2014.02); *G01R 33/5601* (2013.01); *A61M 16/0833* (2014.02); *A61M 16/204* (2014.02); *A61M 16/208* (2013.01); *A61M 2016/003* (2013.01); *A61M 2016/0039* (2013.01); *A61M 2202/0007* (2013.01); *A61M 2202/02* (2013.01); *A61M 2205/3303* (2013.01); *A61M 2230/42* (2013.01)

(58) Field of Classification Search
CPC ............ A61M 31/005; A61M 16/0488; A61M 16/06; A61M 16/0875; A61M 16/202; A61M 16/122; A61M 16/12; A61M 16/0833; A61M 2016/003; A61M 2202/02; A61M 2205/3303; A61M 2230/42; G01R 33/5601; A61B 5/055; A61B 5/0813
USPC ................................................ 600/407–480
See application file for complete search history.

(56) References Cited

U.S. PATENT DOCUMENTS

| | | | | |
|---|---|---|---|---|
| 4,894,013 A | * | 1/1990 | Smith | A61B 8/06 434/268 |
| 5,590,654 A | * | 1/1997 | Prince | A61B 5/411 324/309 |

(Continued)

OTHER PUBLICATIONS

International Search Report dated Aug. 26, 2013 in PCT/US13/39531.

*Primary Examiner* — Sanjay Cattungal
(74) *Attorney, Agent, or Firm* — Baker Botts L.L.P.

(57) ABSTRACT

Systems and methods for delivering a gaseous contrast agent to the lungs of a subject.

17 Claims, 17 Drawing Sheets

Related U.S. Application Data

(60) Provisional application No. 61/642,806, filed on May 4, 2012.

(51) Int. Cl.
| | | |
|---|---|---|
| *A61K 49/08* | (2006.01) | |
| *A61M 16/04* | (2006.01) | |
| *A61M 16/06* | (2006.01) | |
| *A61M 16/08* | (2006.01) | |
| *G01R 33/56* | (2006.01) | |
| A61M 16/20 | (2006.01) | |
| A61M 16/00 | (2006.01) | |

(56) References Cited

U.S. PATENT DOCUMENTS

| | | | |
|---|---|---|---|
| 6,286,319 B1 * | 9/2001 | Hasson | G01R 33/282 |
| | | | 424/9.3 |
| 7,282,032 B2 | 10/2007 | Miller | |
| 7,560,096 B2 | 7/2009 | Driehuys et al. | |
| 7,941,204 B1 | 5/2011 | Wang et al. | |
| 8,161,970 B2 | 4/2012 | Cewers | |
| 2004/0003808 A1 | 1/2004 | Fuhrman et al. | |
| 2010/0042068 A1 * | 2/2010 | Friebe | A61M 5/007 |
| | | | 604/506 |

* cited by examiner

SYSTEM FOR DELIVERY OF GASEOUS IMAGING CONTRAST AGENTS AND METHODS FOR USING SAME

CROSS-REFERENCE TO RELATED APPLICATION

This application is a continuation of PCT/US13/039531, filed May 3, 2013, which claims the benefit of U.S. Provisional Patent Application No. 61/642,806, filed May 4, 2012, both of which are incorporated herein by reference in their entireties.

STATEMENT OF GOVERNMENT SUPPORT

This invention was made with United States government support under Grant R01-HL089064, awarded by the National Institutes of Health. The government has certain rights in this invention.

FIELD

This invention relates to systems and methods for real-time mixing and non-invasive administration of gaseous magnetic resonance imaging (MRI) contrast agents to conscious, spontaneously breathing human subjects inside an MRI scanner.

BACKGROUND

Gaseous contrast agents and, more specifically, hyperpolarized (HP) noble gases, such as helium-3 ($^3$He) and xenon-129 ($^{129}$Xe), are used for investigational imaging of respiratory gas in lungs by MRI for the purpose of assessment of regional lung function. The ultimate goals of such imaging methods include diagnosis, evaluation, and monitoring progression of respiratory diseases, as well as evaluating the efficacy of therapeutic interventions. The pulmonary diseases that can benefit from such an imaging modality include obstructive lung diseases (e.g. emphysema, chronic bronchitis, and asthma) and interstitial lung diseases (e.g. cystic fibrosis and idiopathic pulmonary fibrosis).

HP-gas MRI has enabled pulmonary researchers to investigate different aspects of lung function and structure non-invasively and at a localized level. Stable isotopes of noble gases $^3$He (which, contrary to the natural "balloon" helium, $^4$He, are visible by MRI) and $^{129}$Xe can be polarized through optical pumping with circularly polarized laser light in a machine referred to as a polarizer. They can then be safely inhaled by a human subject lying down inside an MRI scanner (albeit for investigational use only, as this process is not currently approved by the FDA). Images of HP-gas atoms in the airways can then be rapidly acquired by MRI through the direct visualization of respiratory gas distribution in pulmonary airways. The acquirable imaging signal-to-noise ratio (SNR) from HP gases is proportional to their polarization level. The polarization build-up of a HP species is maintained in the polarizer using an external magnetic field (typically a few tens to hundreds of Gauss) and by ensuring a highly clean storage environment (e.g. a baked and evacuated glass cell in the case of $^3$He or a cryogenic trap in the case of $^{129}$Xe). However, the moment HP gas is dispensed from the polarizer, its polarization starts decaying (i.e. relaxes) with a time constant in the order of a few tens of minutes, and therefore it needs to administered and imaged almost immediately. This relaxation rate is even faster in vivo (in the order of a few tens of seconds), primarily due to interactions with other respiratory gas components (most notably the oxygen molecules as discussed further below) and collisions with lung tissue walls.

Generic Applications

Diffusion-weighted HP gas MRI allows for assessing lung microstructure in a similar fashion to CT scans. Single-breath ventilation MRI (also referred to as a spin density map), on the other hand, provides a qualitative picture of respiratory gas distribution in the lungs in a similar fashion to nuclear medicine ventilation scans (e.g., $^{133}$Xe SPECT or $^{13}$N$_2$ PET). Ventilation scans allow for the detection and qualitative evaluation of gross ventilation defects due to airway obstruction or air trapping. Both of these methods can be performed during a short breath-hold (a few seconds) after inhaling a single-breath bolus of HP gas (either with or without oxygen).

Oxygen Tension Imaging

Recently, more sophisticated imaging methodologies have been developed based on HP gas MRI technology to extract richer and more valuable regional information about lung function. At the same time, they pose certain requirements on the delivery pattern and mixture content of the HP gas during the imaging session. Oxygen-weighted HP gas MRI, which is used to measure regional alveolar partial pressure of oxygen ($P_AO_2$), requires real-time mixing of HP $^3$He with oxygen as closely as possible at the normoxic ratio of $^3$He:$O_2 \approx 79:21$. It is necessary to maintain the oxygen content in the inspired gaseous contrast agent at a similar level as normal breathing air (Fraction of Inspired Oxygen ($FiO_2$)=0.21) in order to obtain the most physiologically meaningful alveolar oxygen tension ($P_AO_2$) measurements. However $O_2$ molecules exhibit strong paramagnetic properties (due to the unpaired spins of their outermost two electrons), which in turn leads to a strong dipolar interaction with noble gas species and subsequently causes rapid depolarization (relaxation) of the HP gas. Excessive depolarization of the HP gas is undesirable because it naturally limits the obtainable signal in MR images and will subsequently have a negative effect on the accuracy of quantitative measurements. The depolarization time constant in the case of $^3$He is approximately 20 sec under nominal physiological conditions (body temperature, atmospheric pressure and $O_2$ partial pressure of ~200 mbar). Premature mixing of oxygen and HP noble gas should therefore be avoided if possible. This means that the mixing of the HP gas and oxygen should be performed immediately before the subject inhales the mixture. Since the mixing and inspiration of the mixture may take up to several seconds, there is still a great chance of losing substantial amounts of polarization; up to 30-40% before imaging is performed. It has therefore become customary to keep the HP gas and oxygen components in separate containers (e.g. in specialty plastic bags, divided by the 79:21 volume ratio) separated by a Y-connector and dedicated valves. Immediately before image acquisition, the valves are opened and the subject simultaneously inhales the contents of both bags, thereby minimizing the time that HP gas and oxygen are in contact with each other.

This approach has a major drawback—it does not guarantee that the same proportional amount of HP gas and oxygen is flowing into the lungs throughout the respiratory cycle. For example, the $FiO_2$ can vary substantially (e.g., from 0.10 to 0.30) while depleting the contents of the two bags. Even though the proper amount of gas is stored in each bag, the respiratory effort that the subject applies to the bags and the different tubing resistance between the two flow paths can easily lead to very different flow rates and a varying resulting mixture. This may not initially appear as a major problem, because, given enough time, the subject will eventually inhale the entire contents of both bags before committing a breath-hold for MRI. The non-uniform mixing of the two gases, however, can have a drastic effect on measurements of oxygen tension in the lungs and can drastically skew the $P_AO_2$ values, as has been observed experimentally. For example if the HP $^3$He bag deflates faster than the $O_2$ bag, then the concentration of oxygen in the lung parenchyma of the subject will be lower than normal, whereas the trachea (which was filled later by oxygen) will contain a higher-than-normal oxygen concentration. This induces a non-physiological oxygen gradient in the pulmonary airways, which directly affects the $P_AO_2$ values and would be very difficult or impossible to correct for, especially if the flow ratio information is missing. The proposed device largely eliminates this problem by real-time monitoring and control of the two respiratory gas components (i.e. HP gas and oxygen) while maintaining FiO$_2$ and total volume at the desired levels.

Specific Ventilation Imaging

Another recently developed HP gas MRI method is specific ventilation imaging, which is arguably the only HP gas-based quantitative ventilation imaging technique currently available. This is in contrast to single-breath ventilation imaging, which requires qualitative interpretation by an expert reader. Specific ventilation imaging is based on the delivery of a number of identical HP gas breaths to the subject while acquiring an image of HP gas distribution in the lungs during a short end-inspiratory breath-hold. This idea had been implemented in sedated animals in a fairly straightforward fashion by using a programmable mechanical ventilator. In these implementations, the mechanical ventilator takes control of the respiratory pattern in the sedated and intubated animal, delivers the desired quantity of HP gas mixed with oxygen per breath, commits a breath-hold for image acquisition, and repeats this sequence as many times as desired. In the case of consciously breathing humans, however, such a maneuver is not easily justifiable. A human subject needs to be able to comfortably inhale the HP gas and oxygen mixture through a mask or a mouthpiece and hold his or her breath when reaching the target inspired volume, at which point the images are acquired. The subject should then exhale the gas and continue this pattern at a comfortable breathing rate until the image acquisition sequence is completed (typically over 6-8 breaths).

Accordingly, there is a need in the pertinent art for imaging systems and methods that permit real-time mixing of HP gas and oxygen in order to prevent premature depolarization of the contrast gas while maintaining FiO$_2$ at a normoxic level for the subject's safety. There is a further need in the pertinent art for imaging systems and methods that permit control of the delivered tidal volume ($V_T$) at a specific level in order to image the lung at the same inflation volume over the sequence of several breaths, both for physiological stability and for matching images from different breaths; i.e. image co-registration.

SUMMARY

Described herein is system for delivery of a hyperpolarized gaseous contrast agent to the lungs of a subject. The system includes first and second gas containers for respectively containing a gaseous contrast agent and oxygen gas. The gaseous contrast agent and oxygen gas are selectively delivered to a flow meter, which monitors the flow rate of each respective gaseous component. A flow control valve is provided downstream of the flow meter for selectively providing fluid communication between the flow meter and a delivery tube, which provides the gas mixture to the subject. An imaging device is positioned for imaging of the subject's lungs. A processor is in operative communication with the flow meter, the flow control valve, and the imaging device. The processor selectively opens the flow control valve and selectively activates the imaging device depending upon the flow rates determined by the flow meter. When a desired flow rate and tidal volume have been achieved, the processor synchronizes the opening of the flow control valve and the activation of the imaging device with delivery of the gas mixture to the subject. Methods of using the system are also disclosed.

Additional advantages of the invention will be set forth in part in the description which follows, and in part will be obvious from the description, or may be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DETAILED DESCRIPTION OF THE FIGURES

These and other features of the preferred embodiments of the invention will become more apparent in the detailed description in which reference is made to the appended drawings wherein.

Figures 5A, 5B, 5C:
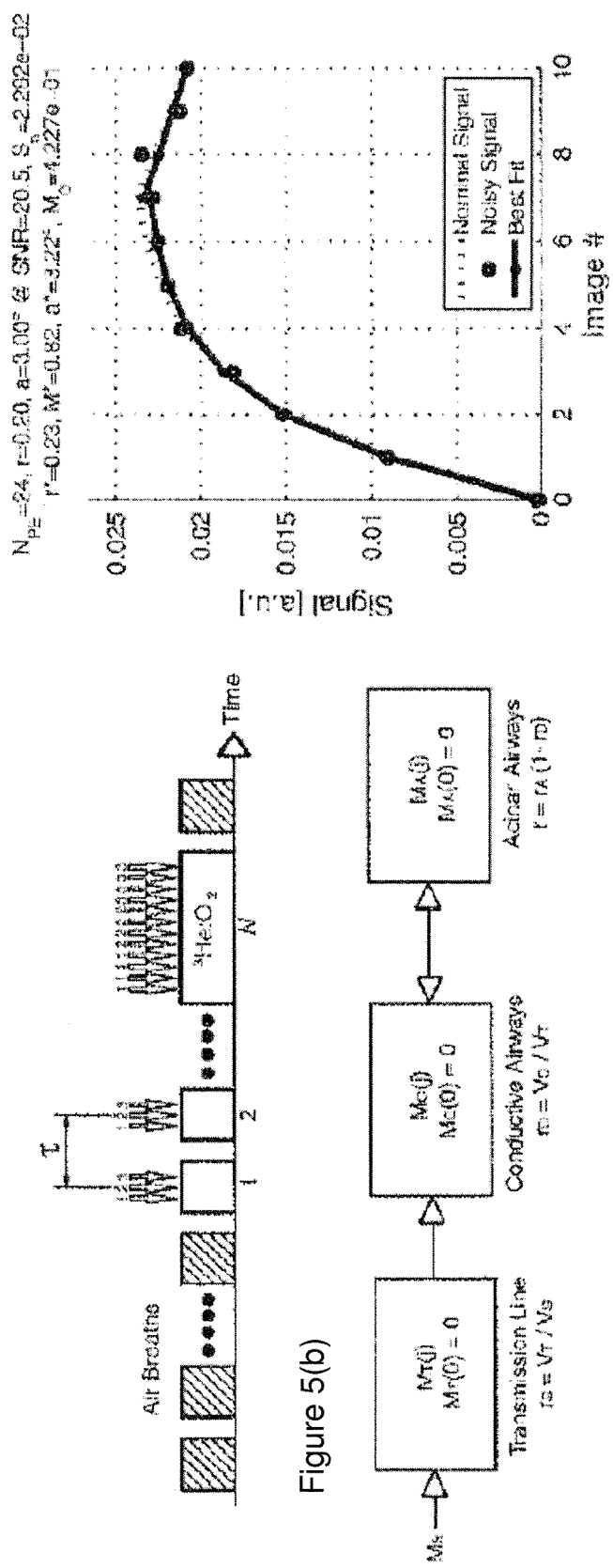

FIG. 5(a) depicts an exemplary multislice fractional ventilation imaging sequence. FIG. 5(b) depicts a three-compartment fractional ventilation model consisting of the static and dynamic dead space volumes $V_S$ and $V_D$. FIG. 5(c) depicts a simulated signal buildup for a representative voxel with nominal r=0.2 and $\alpha$=3°.

Figure 6:
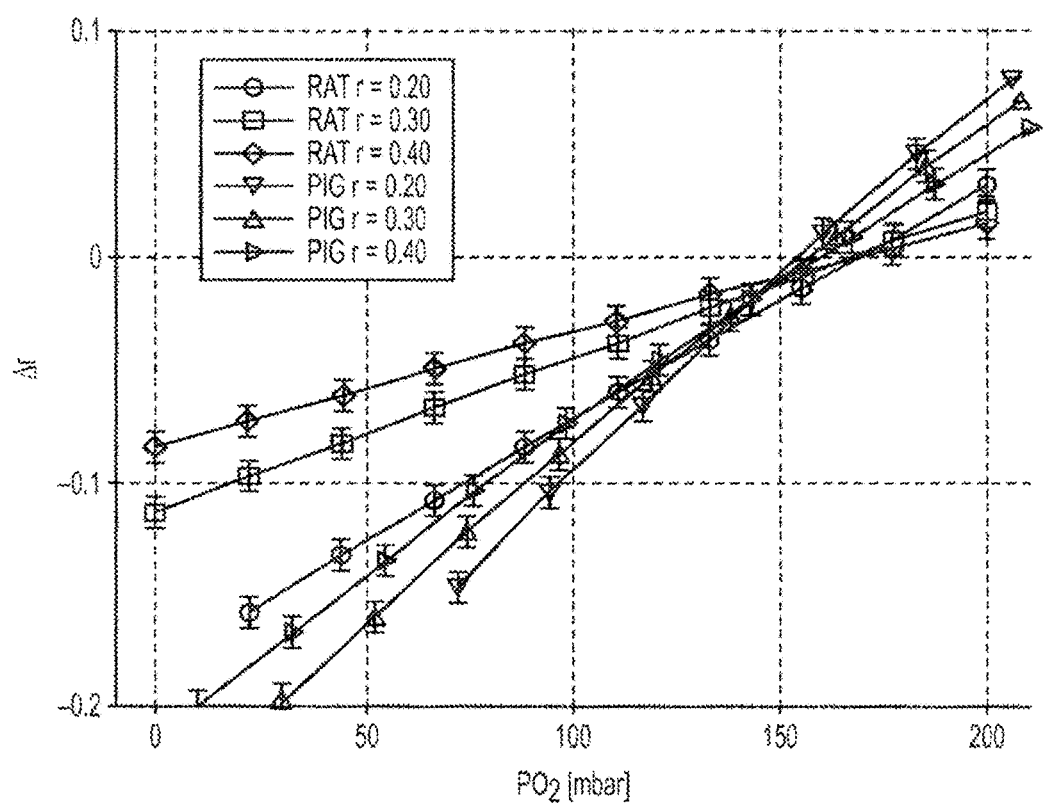

FIG. 6 depicts the systematic error in r estimation as a function of oxygen concentration misassumption in the absence of noise.

Figure 7:
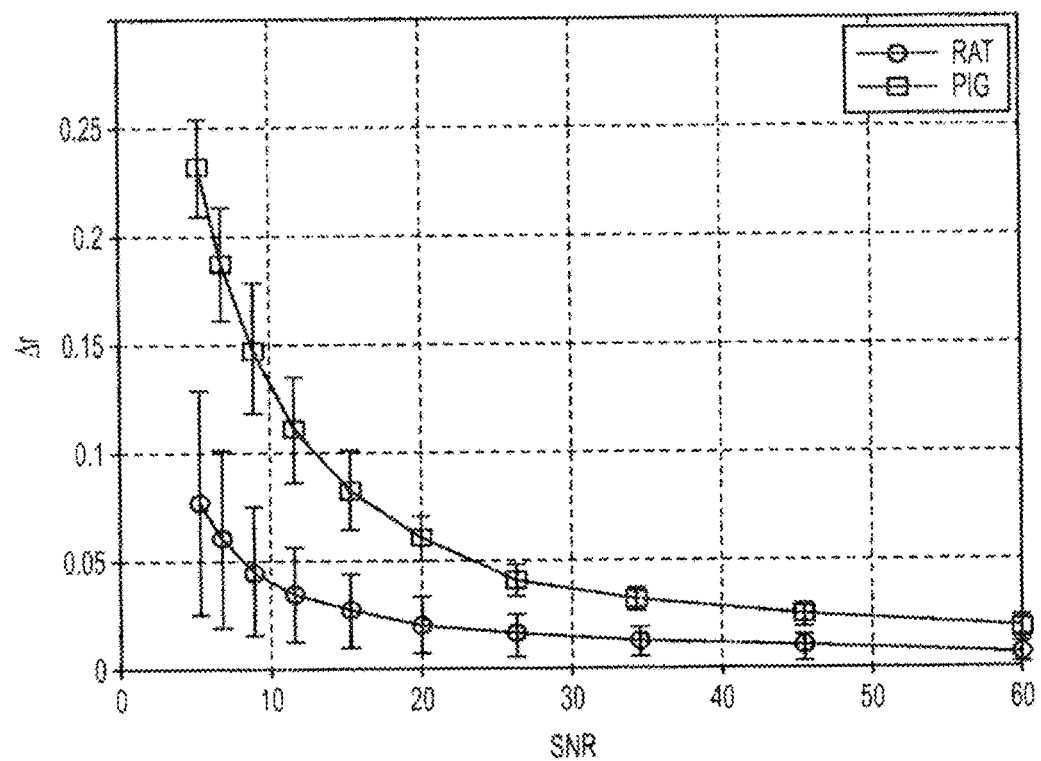

FIG. 7 depicts the relative error in r estimation as a function of the signal-to-noise ratio (SNR) in the second image of a ventilation sequence, assuming a perfect knowledge of $\alpha$.

Figure 8:
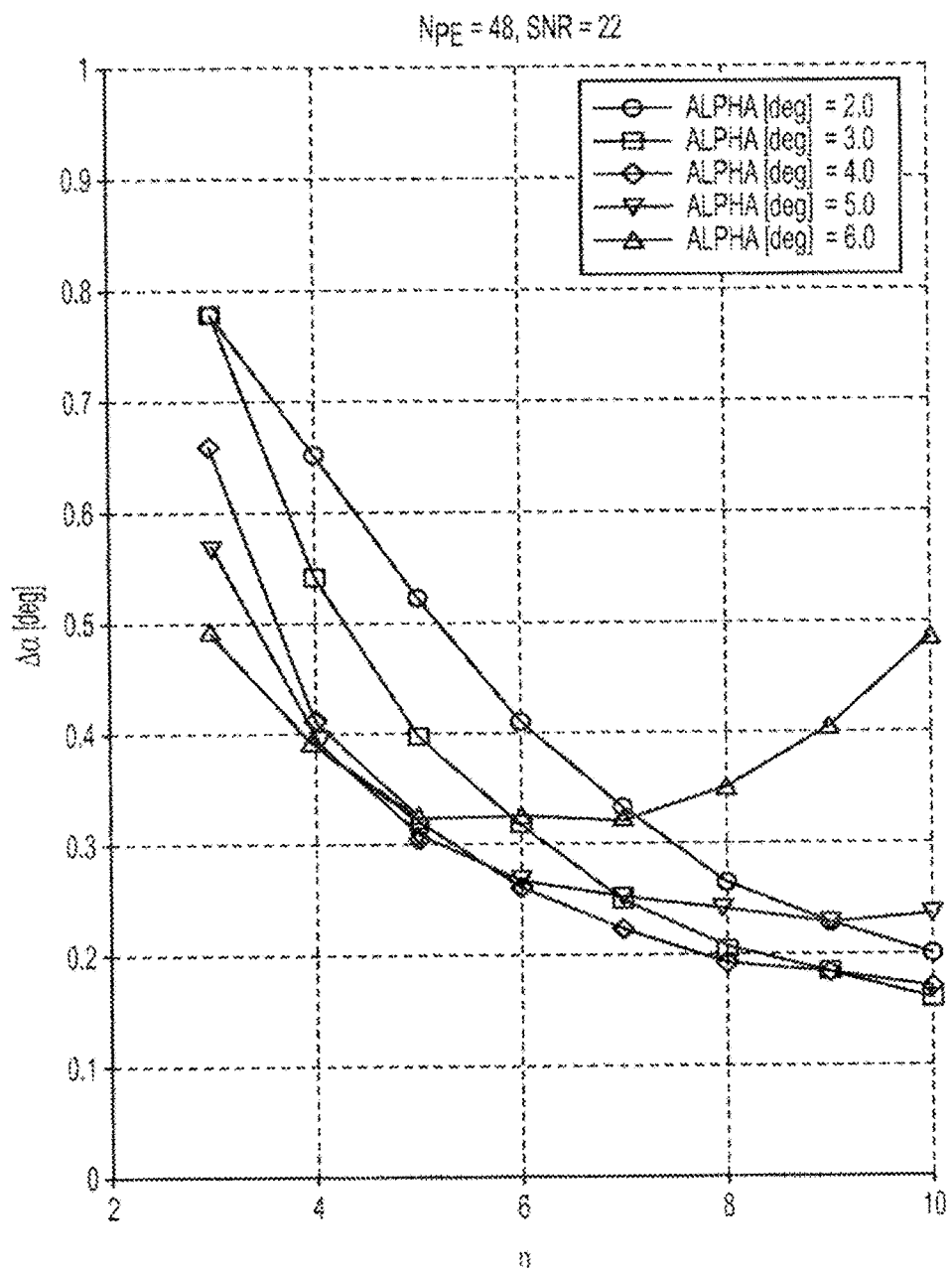

FIG. 8 depicts the relative error in $\alpha$ estimation as a function of the number of sequential images n acquired during an end-inspiratory breath-hold in the ventilation sequence for a typical voxel with an initial SNR=22 and $N_{PE}$=48.

Figure 9:
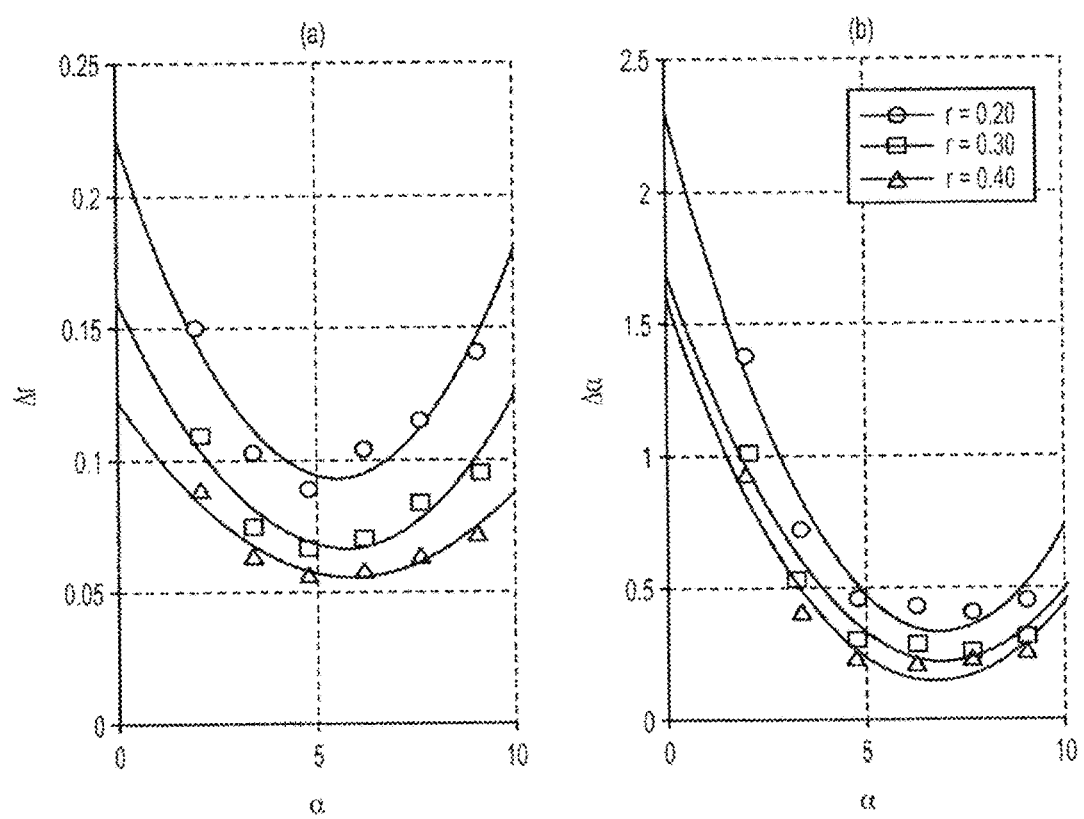

FIG. 9 depicts the reactive error in r and $\alpha$ estimation as a function of the applied $\alpha$ value for a range of radiofrequency (RF) pulses to a single imaging pixel.

Figure 10:
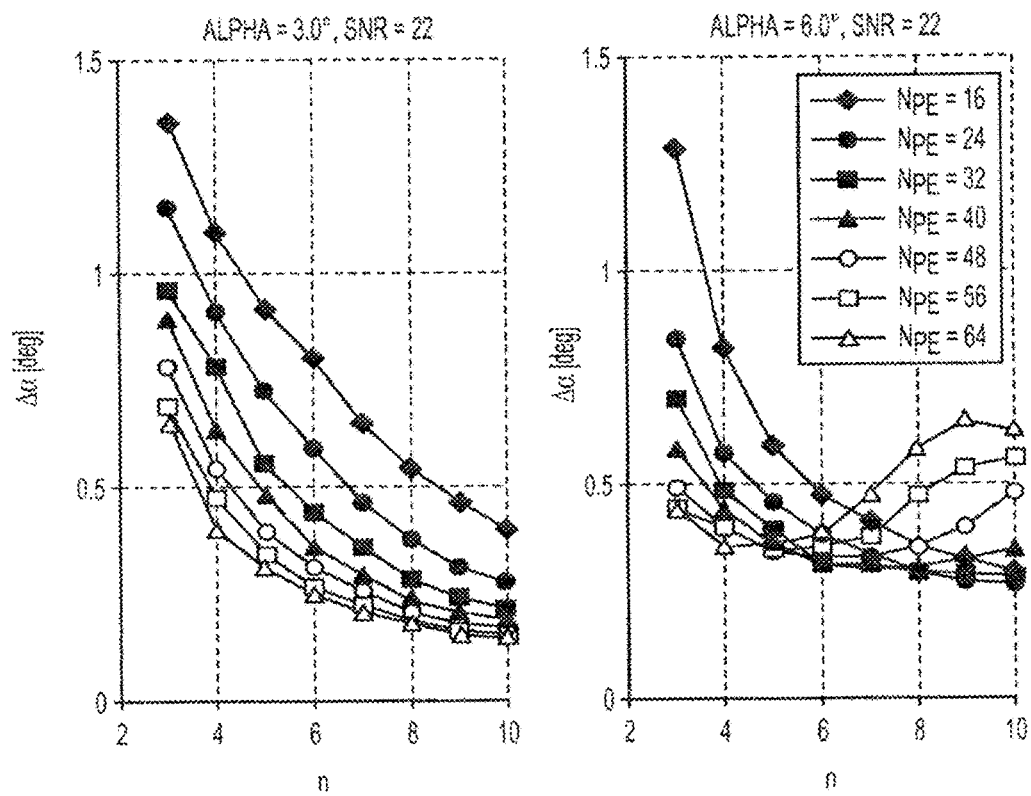

FIG. 10 depicts the relative $\alpha$ error as a function of the number of sequential images (n) acquired during the breath-hold for a single voxel with an initial SNR=22, with the number of RF pulses ranging over 16-64. Two representative flip angles (3° and 6° are shown.

Figure 11:
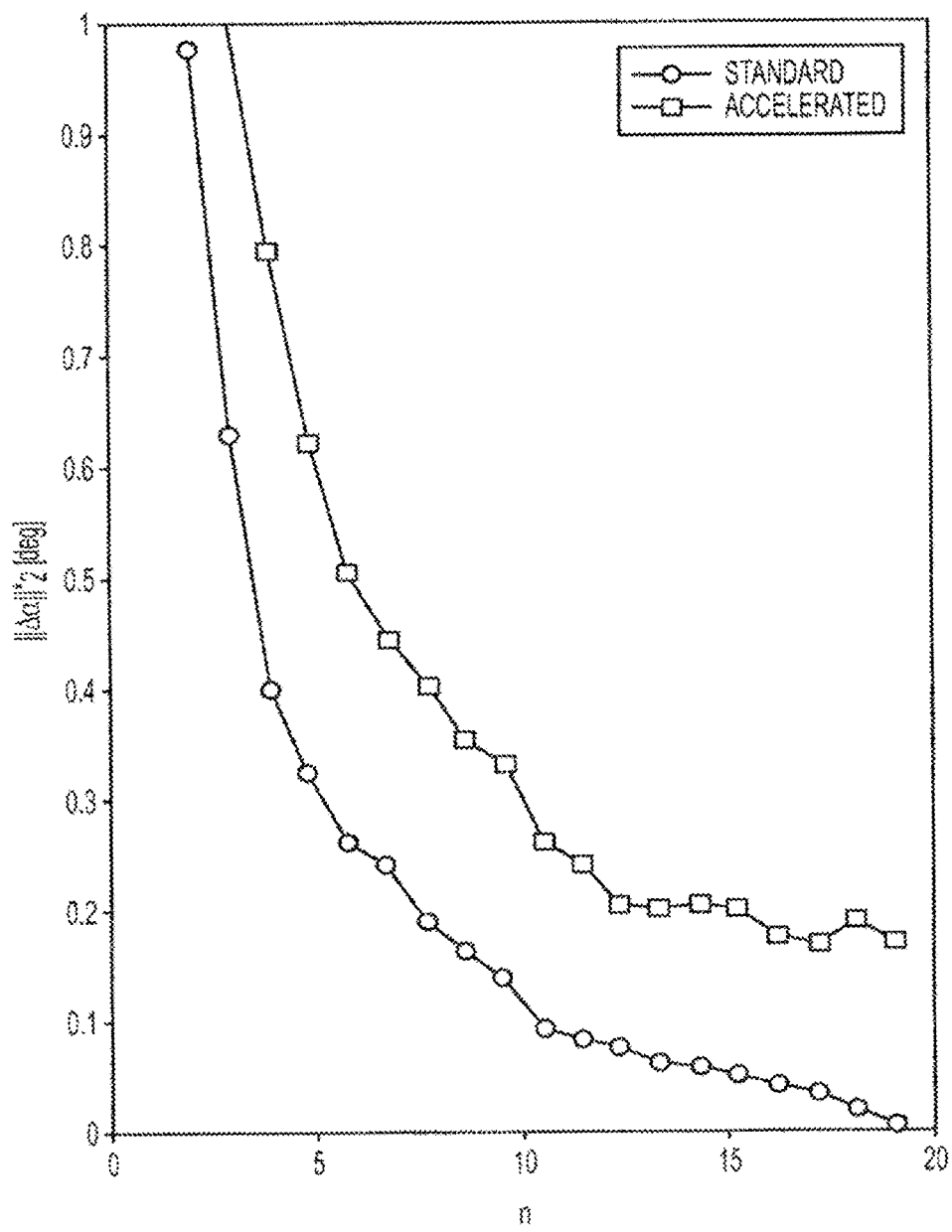

FIG. 11 depicts the variation of α estimation accuracy in a bag phantom using the fully sampled (standard) and undersampled (accelerated) acquisition schemes. The RMS error of a is shown over the entire phantom volume as a function of the number of images, n.

Figure 12A:
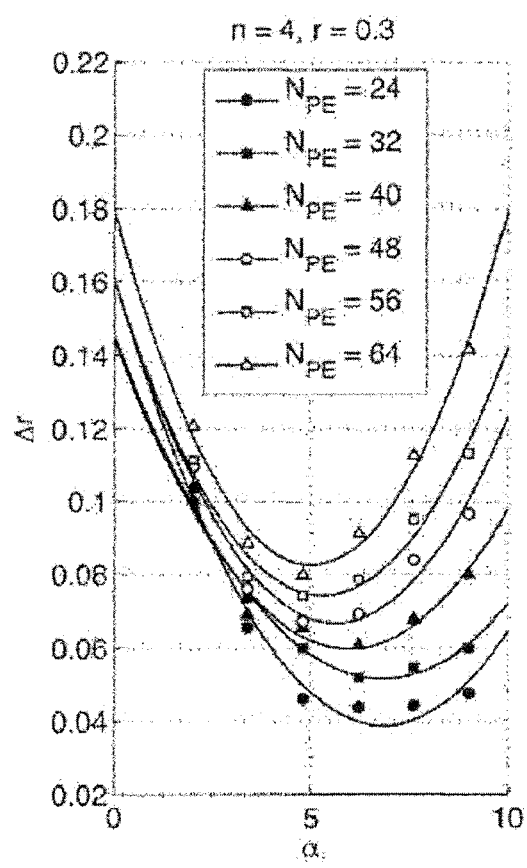
Figure 12B:
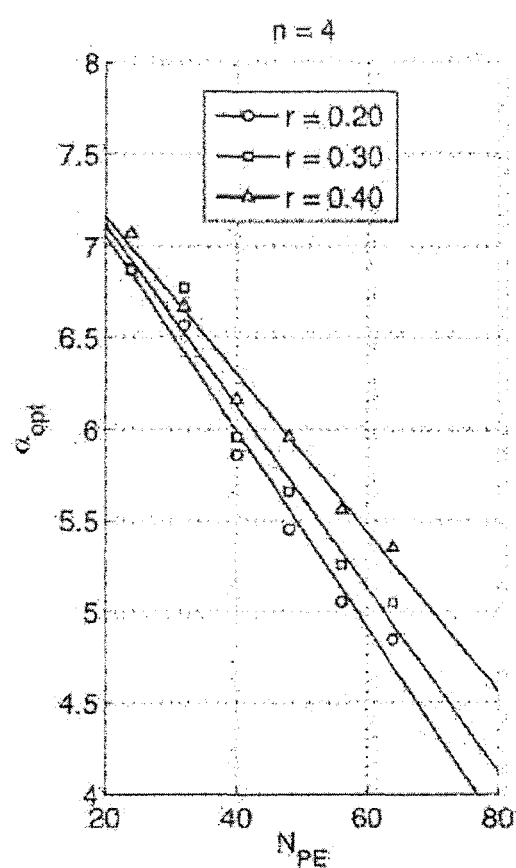

FIG. 12(a) depicts the relative error in r estimation as a function of applied α value for a range of RF pulses (24-64) in a single imaging voxel. FIG. 12(b) depicts the optimal flip angle for r estimation, which exhibits a linear behavior as a function of $N_{PE}$ and is generally independent of r (0.2-0.4).

Figure 13:
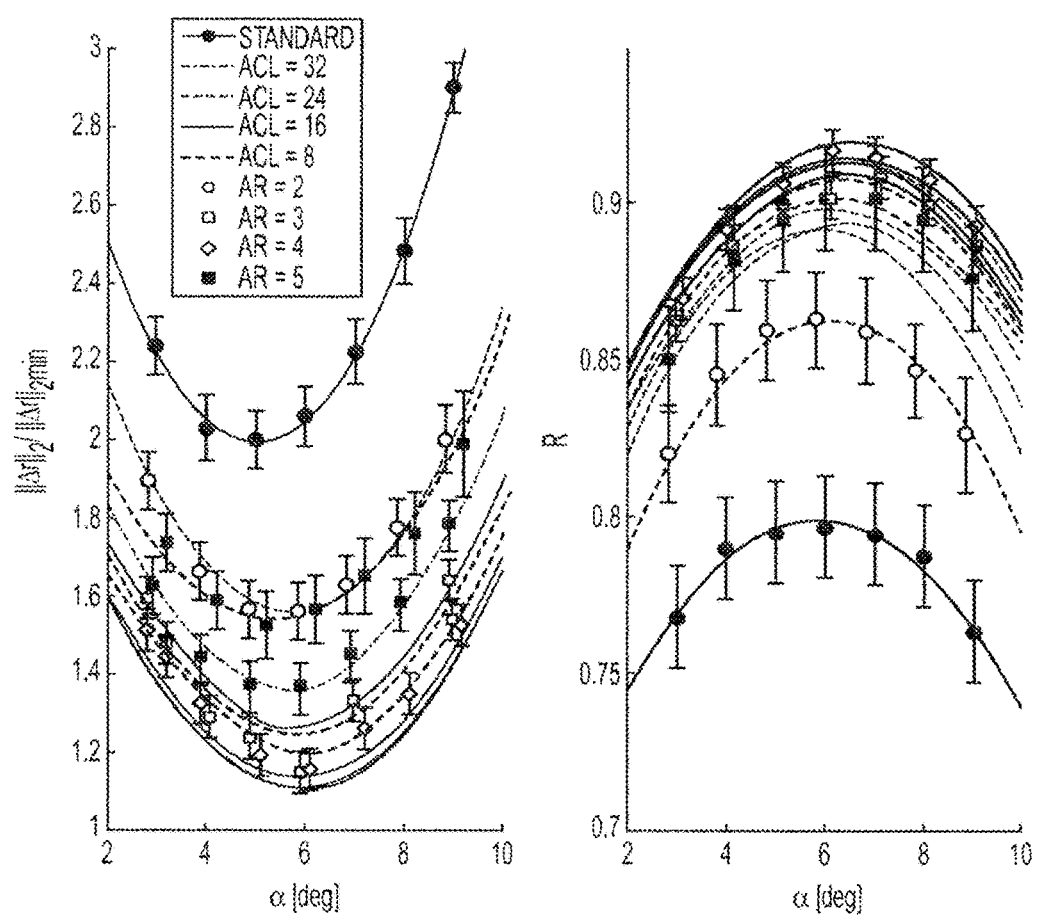

FIG. 13 depicts the accuracy of r estimation in a 64×64 2D image set of pig lungs reconstructed with GRAPPA parallel acceleration using a 4-channel phased array coil.

Figure 14:
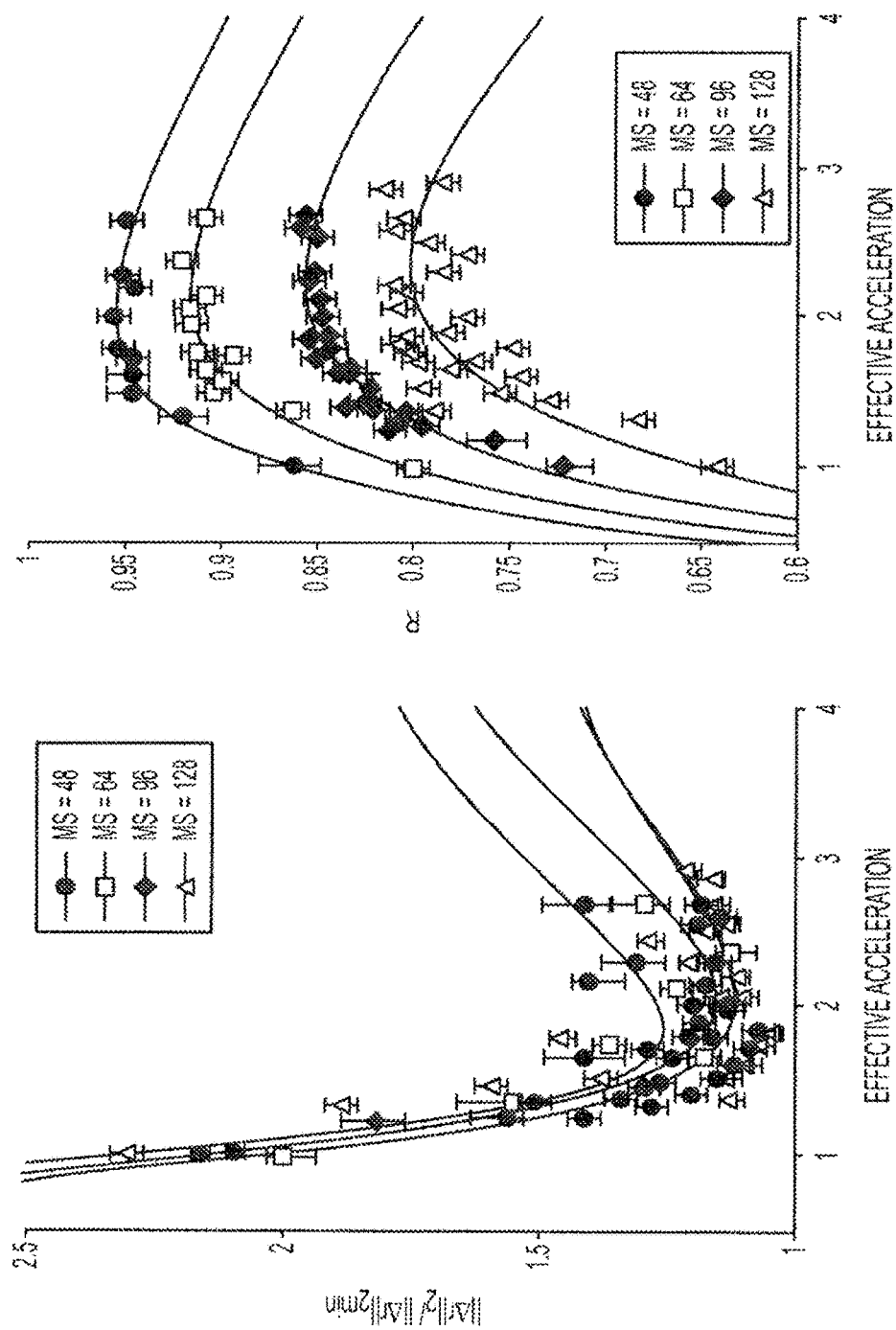

FIG. 14 depicts the variation in RMS error and correlation coefficient as a function of the effective acceleration factor for four different spatial resolutions (MS=48, 64, 96, and 128).

Figure 15:
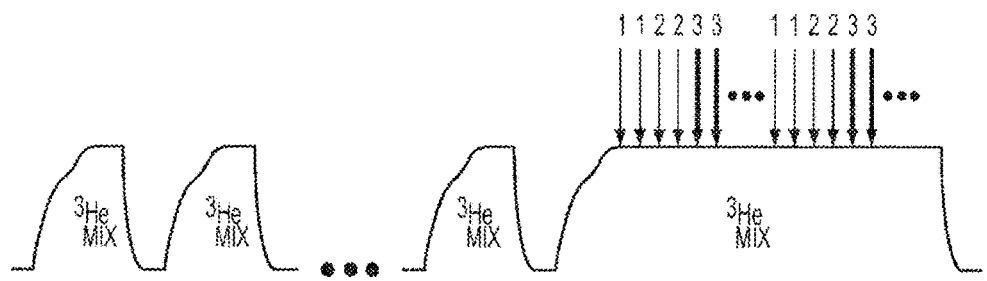

FIG. 15 depicts an exemplary multi-breath $p_AO_2$ imaging protocol. Subjects inhaled a constant volume of imaging gas based on their total lung capacity a couple of times to achieve to a more uniform gas distribution in the lung before the beginning of the $p_AO_2$ imaging. The same amount of gas used in the single-breath imaging can be diluted more with nitrogen.

Figure 16:
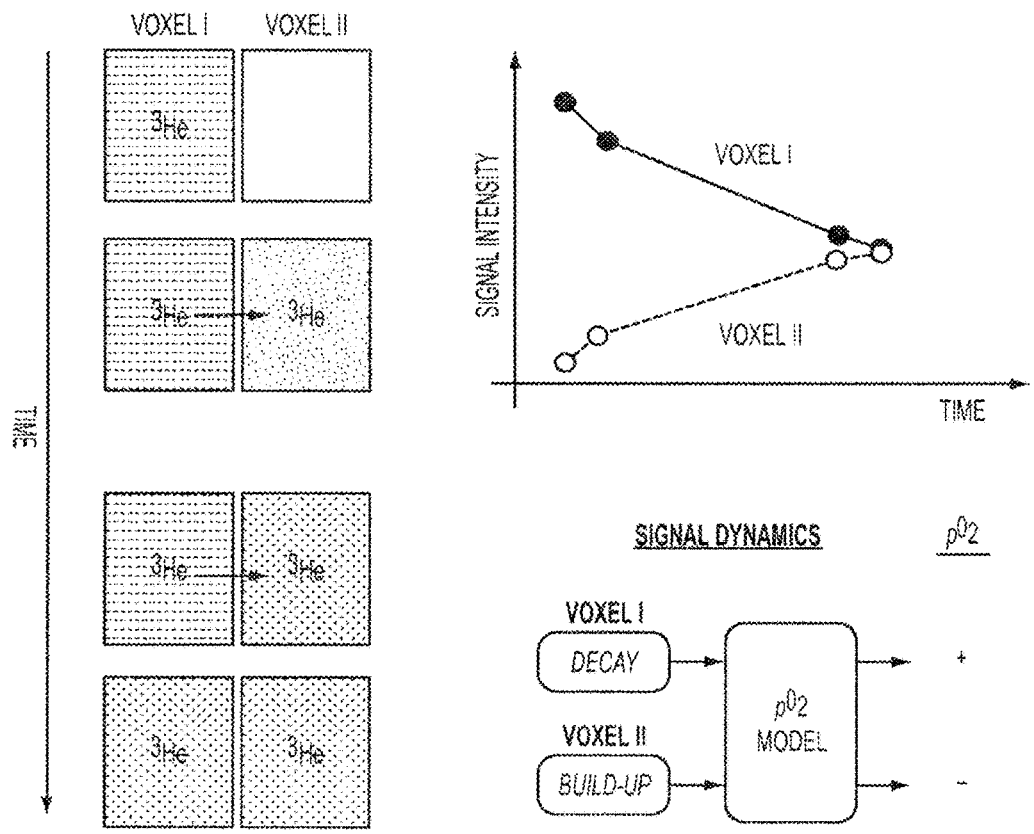

FIG. 16 is graphical representation of exemplary flow artifact in $p_AO_2$ measurements. Slow-filling to a voxel results in a signal build-up which mistakenly can be estimated as a negative $p_AO_2$ and on the other hand the gas escape from a voxel during the imaging can result in a positive error in the $p_AO_2$ value.

Figure 17:
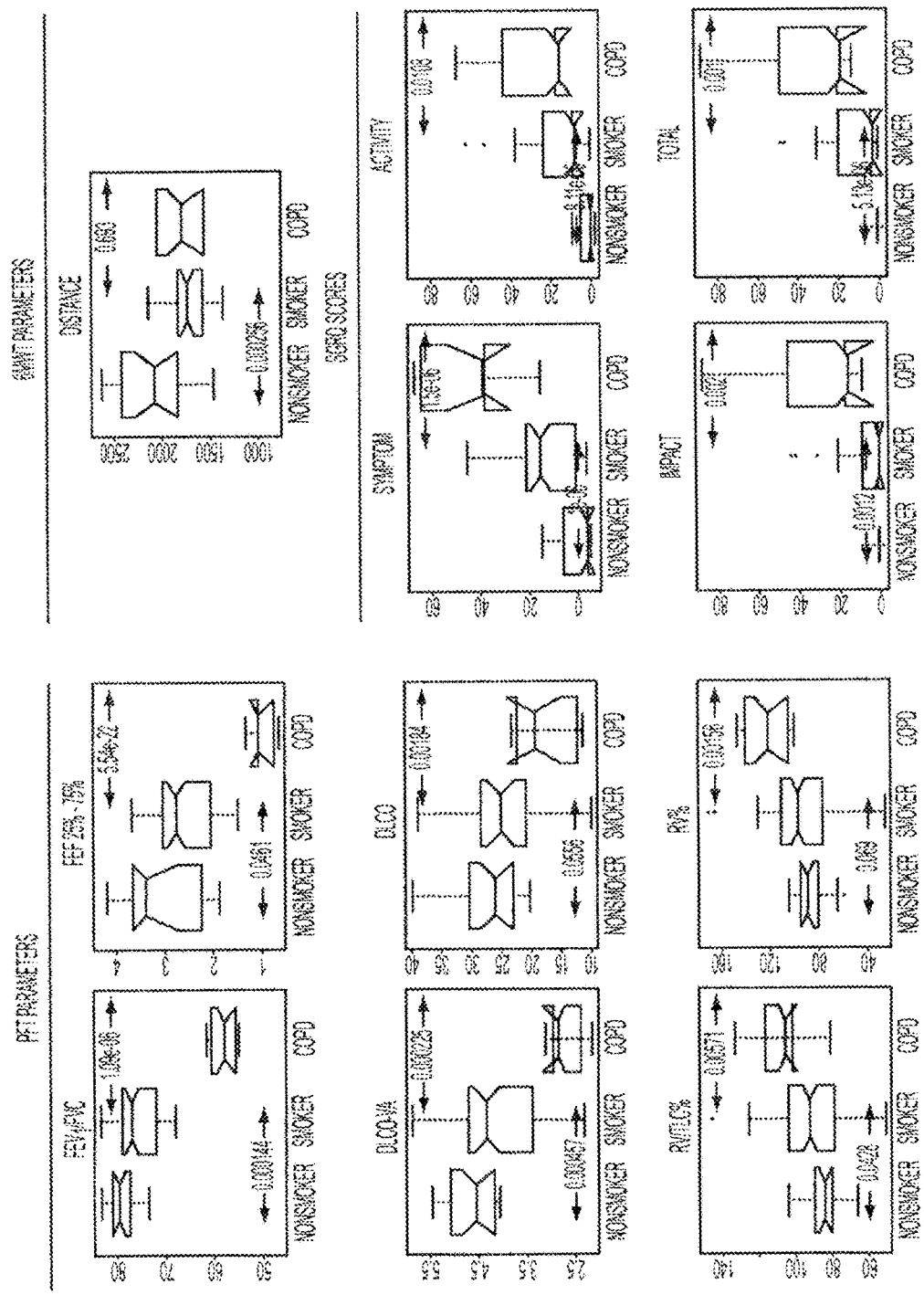

FIG. 17 depicts boxplots of non-imaging parameters (PFT, 6MWT and SGRQ) for each cohort and the results of an ANOVA test's P-values between Nonsmokers and Smokers and between Smokers and COPDs as a measure of the sensitivity of each marker in differentiation between the cohorts. An excellent marker was assumed to have a Pvalue<0.0001 and a good marker to have a P-value<0.001. In the PFTs, the FEV1/FVC and FEF 25%-75% were the excellent markers of COPD. All the SGRQ scores except the Impact, were very sensitive markers of differentiation of Smokers from Nonsmokers and COPDs from Smokers.

Figure 18:
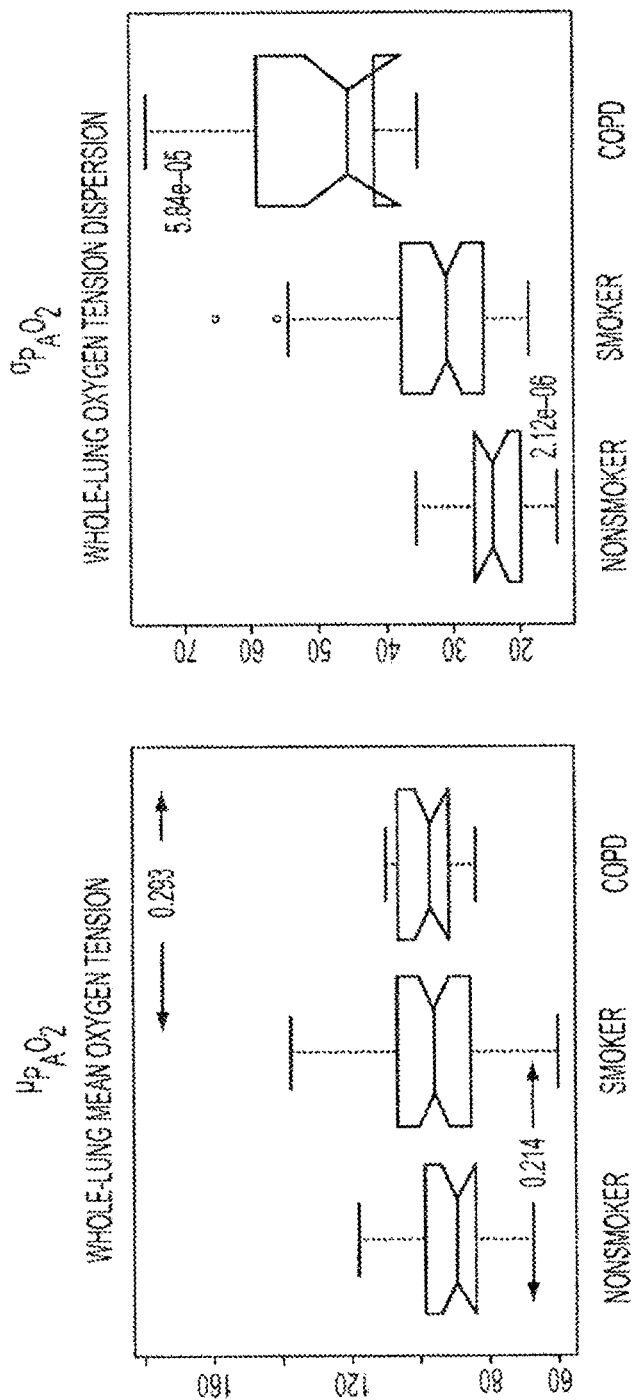

FIG. 18 depicts boxplots of imaging parameters (mean and standard deviation of $p_AO_2$) for each cohort and the results of an ANOVA test's P-values between Nonsmokers and Smokers and between Smokers and COPDs as a measure of the sensitivity of each marker in differentiation between the cohorts. An excellent marker was assumed to have a P-value<0.0001 and a good marker to have a P-value<0.001. The Oxygen Tension Dispersion showed the highest discrimination power among the three cohorts compared to PFT and 6MWT results.

DETAILED DESCRIPTION

The present invention can be understood more readily by reference to the following detailed description, examples, drawings, and claims, and their previous and following description. However, before the present devices, systems, and/or methods are disclosed and described, it is to be understood that this invention is not limited to the specific devices, systems, and/or methods disclosed unless otherwise specified, and, as such, can, of course, vary. It is also to be understood that the terminology used herein is for the purpose of describing particular aspects only and is not intended to be limiting.

The following description of the invention is provided as an enabling teaching of the invention in its best, currently known embodiment. To this end, those skilled in the relevant art will recognize and appreciate that many changes can be made to the various aspects of the invention described herein, while still obtaining the beneficial results of the present invention. It will also be apparent that some of the desired benefits of the present invention can be obtained by selecting some of the features of the present invention without utilizing other features. Accordingly, those who work in the art will recognize that many modifications and adaptations to the present invention are possible and can even be desirable in certain circumstances and are a part of the present invention. Thus, the following description is provided as illustrative of the principles of the present invention and not in limitation thereof.

As used throughout, the singular forms "a," "an" and "the" include plural referents unless the context clearly dictates otherwise. Thus, for example, reference to "a splint" can include two or more such splints unless the context indicates otherwise.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

As used herein, the terms "optional" or "optionally" mean that the subsequently described event or circumstance may or may not occur, and that the description includes instances where said event or circumstance occurs and instances where it does not.

The word "or" as used herein means any one member of a particular list and also includes any combination of members of that list.

As used herein, a "subject" is an individual and includes, but is not limited to, a mammal (e.g., a human, horse, pig, rabbit, dog, sheep, goat, non-human primate, cow, cat, guinea pig, or rodent), a fish, a bird, a reptile or an amphibian. The term does not denote a particular age or sex. Thus, adult and newborn subjects, as well as fetuses, whether male or female, are intended to be included. A "patient" is a subject afflicted with a disease or disorder. The term "patient" includes human and veterinary subjects. As used herein, the term "subject" can be used interchangeably with the term "patient."

Described herein are systems and methods for delivering a gaseous contrast agent to the lungs of a subject for purposes of imaging the lungs of the subject. It is contemplated that the described systems can permit real-time monitoring and control of at least two respiratory gas components (such as, for example, a hyperpolarized gaseous contrast agent and oxygen gas) while maintaining a desired fraction of inspired oxygen ($FiO_2$) and a desired total volume of respiratory gas (to maintain a desired tidal volume). It is further contemplated that the described systems can be configured to trigger an imaging device, such as an MRI scanner, to acquire images of the lungs of the subject at an appropriate time during the course of a single breath and/or across a multi-breath sequence.

In exemplary aspects, the described systems can be configured for safe operation in a magnetic field of up to at least 3 Tesla, with the components of the system being placed or configured such that there is no interference with magnetic field gradients during image acquisition. It is contemplated that the disclosed systems can be operated in a passive manner, with the system configured to respond to the voluntary respiratory effort of the subject, thereby minimizing and/or eliminating the need for supervision during the methods described herein. Additionally, it is contemplated that these passive operation capabilities can provide higher levels of comfort of the subject by permitting the subject to breathe at a desired inspiratory-expiratory rate.

It is further contemplated that the described systems can also produce a negligible ventilation dead space, thereby minimizing re-breathing of expired gases and enhancing accuracy of quantitative oxygen and ventilation MRI measurements. This negligible ventilation dead space can promote efficient use of the finite amount of hyperpolarized gaseous contrast agents that are typically available during an imaging session. It is contemplated that the described systems can be programmable with user-specific gas delivery and imaging parameters. In exemplary systems, the tidal volume, gas concentration, and image triggering can be selectively adjusted for a given subject based upon previously obtained subject-specific data. During use of the described systems, image acquisition is preferably synchronized with the respiratory pattern of the subject. Further, it is contemplated that the described system can be capable of recapturing enriched rare isotopes, such as, for example, $^3$He and $^{129}$Xe, for recycling and purification.

Figure 1:
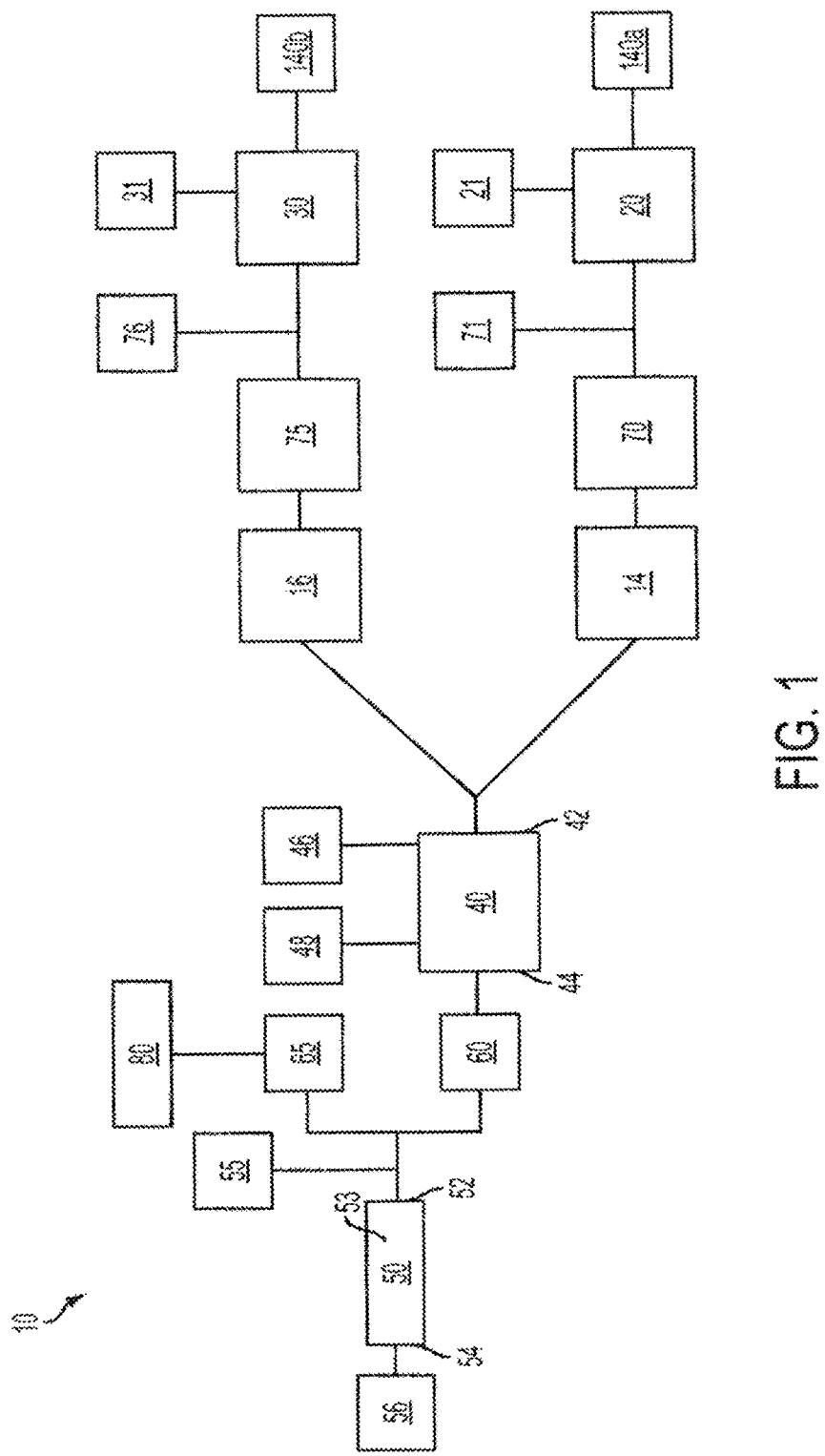
FIG. 1 is a schematic diagram of an exemplary gas delivery system as disclosed herein.
Figure 2:
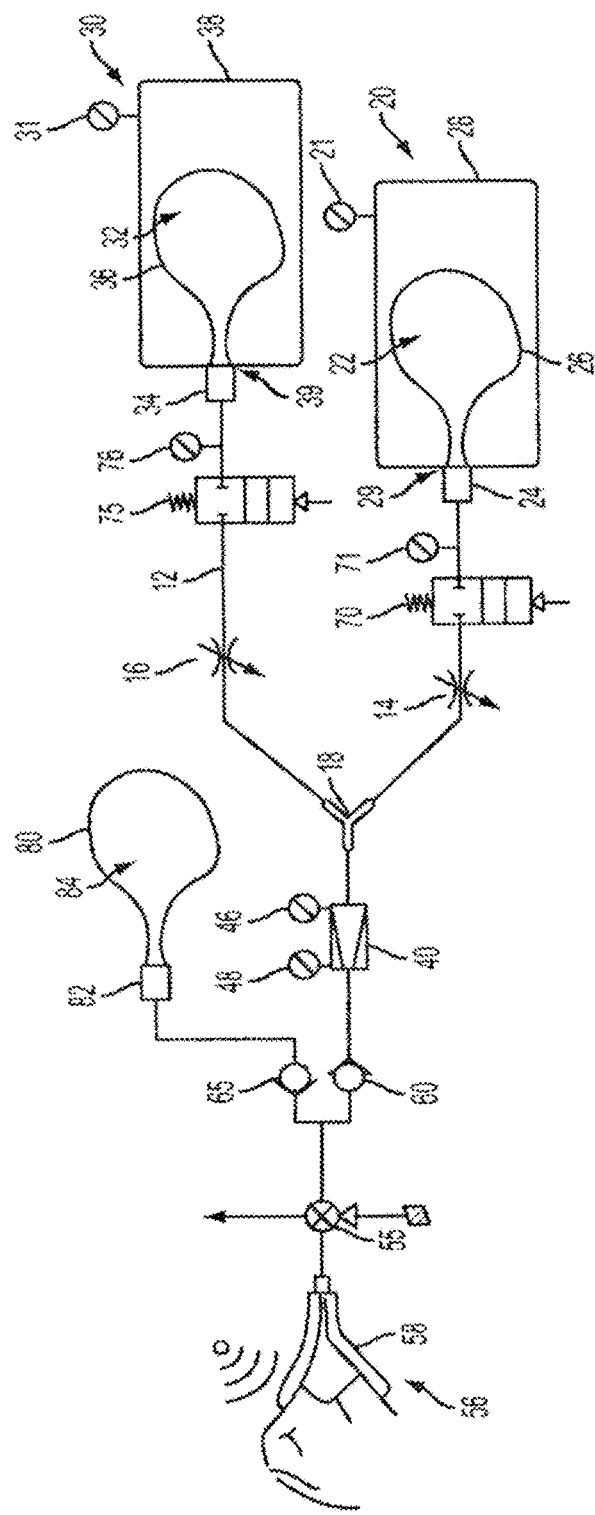
FIG. 2 is a schematic diagram of an exemplary gas delivery system as disclosed herein.
Figure 3A:
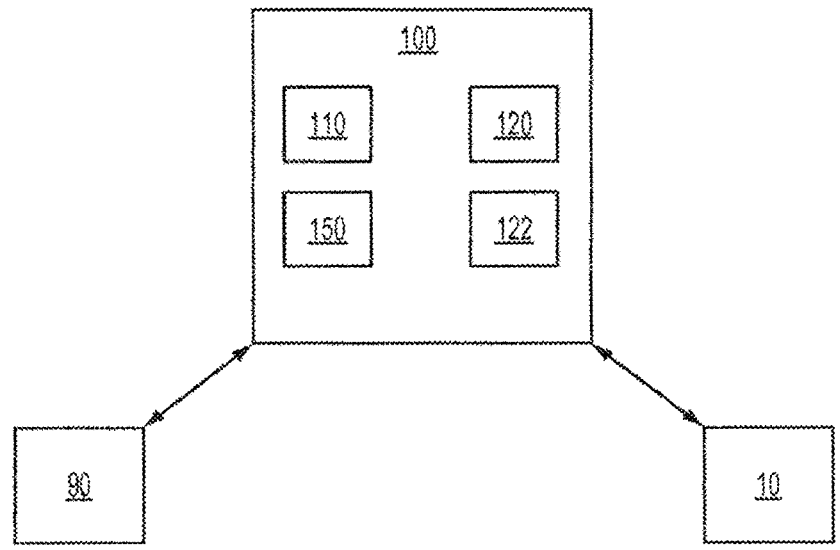
FIG. 3A is a schematic diagram showing an exemplary interaction between a computer having a processor and the components of a gas delivery system as disclosed herein.

In one aspect, and with reference to FIGS. 1-3, the system 10 for delivery of a gaseous contrast agent to the lungs of a subject can comprise a first gas container 20 and a second gas container 30. In this aspect, the first gas container 20 can define an interior volume 22 that is configured to contain the gaseous contrast agent. It is contemplated that the gaseous contrast agent can comprise a hyperpolarized gaseous contrast agent, such as, for example and without limitation, $^3$He and $^{129}$Xe. It is further contemplated that the first gas container 20 can have an outlet 24 in fluid communication with the interior volume 22 of the first gas container.

The second gas container 30 can define an interior volume 32 that is configured to contain oxygen gas. It is contemplated that the second gas container 30 can have an outlet 34 in fluid communication with the interior volume 32 of the second gas container. It is contemplated that the gas containers 20, 30 can comprise any material that is capable of retaining a selected gas.

In exemplary aspects, the first gas container can comprise a first reservoir bag 26, and the second gas container can comprise a second reservoir bag 36. In these aspects, it is contemplated that the first reservoir bag 26 can define the outlet 24 and the interior volume 22 of the first gas container. It is further contemplated that the second reservoir bag 36 can define the outlet 34 and the interior volume 32 of the second gas container. It is contemplated that the reservoir bags 26, 36 can comprise any conventional bag-like structure that is configured to receive and retain a gas. In exemplary aspects, it is contemplated that the reservoir bags 26, 36 can be a Tedlar plastic bag as are known in the art.

In additional exemplary aspects, as shown in FIG. 2, the first gas container 20 can further comprise a first chamber 28, and the second gas container 30 can further comprise a second chamber 38. In these aspects, the first chamber 28 can be configured to receive at least a portion of the first reservoir bag 26, and the second chamber 38 can be configured to receive at least a portion of the second reservoir bag 36. It is contemplated that the first chamber 28 and the second chamber 38 can define respective openings 29, 39. It is further contemplated that at least a portion of the outlet 24 of the first reservoir bag 26 can be received within the opening 29 of the first chamber 28. It is still further contemplated that at least a portion of the outlet 34 of the second reservoir bag 36 can be received within the opening 39 of the second chamber 38. In exemplary aspects, it is contemplated that the first and second chambers 28, 38 can comprise plastic.

In exemplary aspects, the first and second chambers 28, 38 can be configured to receive a selected gas, such as, for example and without limitation, an inert gas. In these aspects, it is contemplated that an inert (or other) gas can surround the reservoir bag and be selectively pressurized to maintain a desired pressure on the reservoir bag within the chamber. Thus, it is contemplated that the gas within the respective chambers can be selectively pressurized to ensure that gas exits the respective reservoir bags at a suitable rate and volume, thereby maintaining an appropriate distribution within the gas mixture delivered to the subject. Optionally, in further aspects, it is contemplated that the first and second chambers 28, 38 can be in fluid communication with respective pressure transducers 21, 31 for measuring the pressure within each chamber. In still further aspects, it is contemplated that the first and second chambers 28, 38 can be in fluid communication with an external gas source 140*a*, 140*b* for providing pressurized gas to each chamber. In these aspects, it is contemplated that each chamber 28, 38 can comprise conventional valving and/or tubing for receiving pressurized gas from the external gas sources 140*a*, 140*b*.

Optionally, in further aspects, it is contemplated that one or more secondary chambers can be positioned in fluid communication with one or more of the first gas container 20 and the second gas container 30 to reduce the fluctuation of internal pressure as HP gas is depleted during an imaging process as disclosed herein.

In another aspect, the system 10 can comprise a flow meter 40 having an inlet 42 and an outlet 44. In this aspect, the inlet 42 of the flow meter 40 can be in fluid communication with the outlets 24, 34 of the first and second gas containers 20, 30. It is contemplated that the inlet 42 of the flow meter 40 can be in fluid communication with the outlets 24, 34 of the first and second gas containers 20, 30 such that the flow meter receives a mixture of the gaseous contrast agent and the oxygen gas stored respectively in the first and second gas containers. In an additional aspect, the flow meter 40 can be configured to produce a first flow signal indicative of the flow rate of the gaseous contrast agent within the flow meter and a second flow signal indicative of the flow rate of the oxygen gas within the flow meter. In exemplary aspects, the flow meter 40 can comprise a pneumotachometer. In these aspects, it is contemplated that the flow meter 40 can comprise first and second pressure transducers 46, 48, with the first pressure transducer 46 being configured to produce a first pressure signal indicative of the pressure of the gas as it enters the flow meter and the second pressure transducer 48 being configured to produce a second pressure signal indicative of the pressure of the gas as it exits the flow meter. It is further contemplated that the flow rate can be determined based upon the differential pressure observed by the first and second pressure transducers 46, 48.

In a further aspect, the system 10 can comprise a delivery tube 50 defining a central bore 53 and having a first end 52 and an opposed second end 54. In this aspect, the second end 54 of the delivery tube 50 can be configured for coupling to the mouth of the subject. Optionally, as shown in FIG. 1, the system can comprise an interface component 56 coupled to the second end of the delivery tube 50 and configured for operative coupling to the mouth of the subject. For example, it is contemplated that the interface component 56 can be a mouthpiece. Alternatively, as shown in FIG. 2, it is contemplated that the subject interface component 56 can be a facemask 58. Optionally, in exemplary aspects, it is contemplated that the interface component 56 can comprise at least one of a mouthpiece and a facemask. In further exemplary aspects, as shown in FIG. 2, it is contemplated that an exhaust valve 55 can be positioned between the flow meter 40 (or fluid control valves 60, 65, as further disclosed herein) and the delivery tube 50.

In yet another aspect, the system 10 can comprise a first flow control valve 60 positioned between, and in fluid communication with, the outlet 44 of the flow meter 40 and the first end 52 of the delivery tube 50. In this aspect, the first flow control valve 60 can be configured to provide selective fluid communication between the outlet 44 of the flow meter 40 and the first end 52 of the delivery tube 50.

In various aspects, it is contemplated that the various components of the system 10 can be operatively connected to each other using conventional tubing 12, as shown in FIG. 2. Optionally, in exemplary aspects, as shown in FIG. 2, the system 10 can comprise a conventional Y-connector 18 configured to receive the gases released from each respective gas containers 20, 30 (and fluid control valves 70, 75) and to direct the gases into the flow meter 40. In between the fluid control valves 70, 75 and the Y-connector 18, it is contemplated that the system 10 can further comprise throttle valves 14, 16 as shown in FIG. 2. It is contemplated that these throttle valves 14, 16 can be used to selectively restrict flow of gas between the gas containers 20, 30 (and fluid control valves 70, 75) and the flow meter 40.

In still another aspect, as shown in FIG. 3, the system 10 can comprise an imaging device 90. In this aspect, it is contemplated that the imaging device 90 can be, for example and without limitation, a magnetic resonance imaging (MRI) machine. In exemplary aspects, the materials of the various components of the system can be compatible with the imaging device. Thus, when the imaging device comprises a MRI machine, it is contemplated that the components of the system positioned proximate the subject can be non-magnetic so as to avoid interference with the MRI machine. For example, it is contemplated that the various flow control valves within the system can comprise pneumatic flow control valves. However, it is understood that certain system components that would interfere with MRI imaging can be positioned in a location where interference is avoided.

In an additional aspect, the system 10 can comprise a processor 110. In this aspect, it is contemplated that the processor 110 can be provided as part of a conventional computer 100. In exemplary aspects, it is contemplated that the computer 100 can further comprise at least one interface module 120 to ensure operative communication between the processor 110 and the imaging device 90 and/or the other elements the disclosed system 10. In these aspects, it is further contemplated that the computer 100 can comprise a data acquisition (DAQ) unit as is known in the art. The DAQ unit can be positioned in operative communication with the at least one interface module 120 and/or the processor 110. In a further aspect, the computer 100 can comprise a memory 150 positioned in operative communication with the processor 110.

In this aspect, the processor 110 can be positioned in operative communication with the flow meter 40, the first flow control valve 60, and the imaging device 90. It is contemplated that the processor 110 can be configured to receive the first and second flow signals from the flow meter 40. It is further contemplated that the processor 110 can be configured to selectively open the flow control valve 60 in response to the first and second flow signals. It is still further contemplated that the processor 110 can be configured to selectively activate the imaging device 90 in response to the first and second flow signals. In exemplary aspects, the processor 110 can be configured to determine a monitored flow ratio corresponding to the ratio of oxygen gas to gaseous contrast agent within the flow meter 40. In these aspects, the processor 110 can be configured to compare the monitored flow ratio to a desired flow ratio, such as, for example, a flow ratio corresponding to the $FiO_2$ fraction to be maintained during the imaging sequence.

In order to provide for volumetric control of the gaseous mixture that is delivered to the flow meter 40 (and, ultimately, provided to the subject), the system 10 can further comprise (a) a first pressure valve 70 positioned between, and in fluid communication with, the outlet 24 of the first gas chamber 20 and the inlet 42 of the flow meter 40 and (b) a second pressure valve 75 positioned between, and in fluid communication with, the outlet 34 of the second gas chamber 30 and the inlet 42 of the flow meter 40. The first and second pressure valves 70, 75 can be configured to provide selective fluid communication between the respective outlets 24, 34 of the first and second gas containers 20, 30 and the inlet 42 of the flow meter 40.

In exemplary aspects, the processor 110 can be in operative communication with the first and second pressure valves 70, 75. In these aspects, the processor 110 can be configured to selectively open the first and/or second pressure valves 70, 75 such that a selected volume of the gaseous contrast agent and/or the oxygen gas enters the inlet 42 of the flow meter 40. In these aspects, it is contemplated that the total volume of the selected volumes of the gaseous contrast agent and the oxygen gas can substantially correspond to a tidal volume of the lungs of the subject.

Optionally, in other exemplary aspects, the processor can be in operative communication with the throttle valves 14, 16 to selectively restrict flow of gas between the pressure valves 70, 75 and the flow meter 40.

Optionally, in still other exemplary aspects, the processor 110 can be in operative communication with the pressure transducers 21, 31 in communication with the first and second chambers 28, 38. In these aspects, it is contemplated that the pressures within each chamber can be continuously monitored. In further aspects, it is contemplated that the processor 110 can be in operative communication with one or more of the external gas sources 140a, 140b such that the processor can be configured to selectively provide pressurized gas to the first and second chambers 28, 38. Thus, it is contemplated that the processor 110 can be configured to selectively adjust the pressure within each respective chamber 28, 38. For example, in use, the processor 110 can be used to re-pressurize the chambers in order to compensate for the non-linear behavior of shrinking reservoir bags, differences in line resistance, and/or drifts in system performance over time.

Preferably, the processor 110 can be configured to open the first pressure valve 70, the second pressure valve 75, and the first flow control valve 60 such that delivery of the mixture of gaseous contrast agent and oxygen gas is synchronized with inspiration by the subject and/or a sequence of inspirations by the subject. Similarly, it is contemplated that the processor 110 can be further configured to synchronize activation of the imaging device 90 with inspiration by the subject.

In another aspect, the system 10 can further comprise a collection container 80 defining an interior space 84 and having an inlet 82 in fluid communication with the first end 52 of the delivery tube 50. In this aspect, it is contemplated that the collection container 80 can be configured to receive expired gases from the subject.

In a further aspect, the system 10 can comprise a second flow control valve 65 positioned between, and in fluid communication with, the first end 52 of the delivery tube 50 and the inlet 82 of the collection container 80. In this aspect, the second flow control valve 65 can be configured to provide selective fluid communication between the delivery tube 50 and the inlet 82 of the collection container 80. Optionally, the processor 110 can be in operative communication with the second flow control valve 65. It is contemplated that the processor 110 can be configured to selectively open the second flow control valve 65. It is further contemplated that the processor 110 can be configured to synchronize the opening of the second flow control valve 65 with expiration by the subject.

Although described herein as comprising first and second containers, it is contemplated that the system 10 can further comprise one or more additional gas containers as disclosed herein for selectively delivering a gas to a subject. Thus, for example, it is contemplated that a third gas container can be positioned in fluid communication with the first and second gas containers 20, 30. Similarly, it is contemplated that the system 10 can optionally comprise additional flow control valves and/or pressure transducers that are positioned in fluid communication with the additional gas containers. It is still further contemplated that the processor 110 can be positioned in operative communication with the additional flow control valves and/or pressure transducers.

Figure 3B:
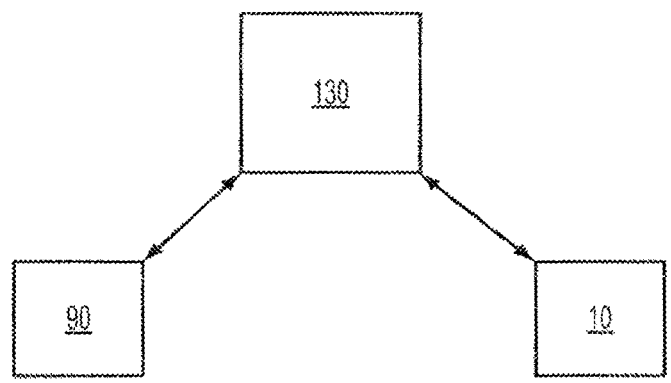
FIG. 3B is a schematic diagram showing an exemplary interaction between a microcontroller and the components of a gas delivery system as disclosed herein.

As shown in FIG. 3B, it is contemplated that all software and hardware functionalities disclosed herein can be combined into a compact embedded microcontroller 130, thereby eliminating the need for a dedicated computer and DAQ card, if desired.

In use, the system 10 can initially be calibrated for a particular subject. It is contemplated that a distinct gas mixture (different from the gaseous contrast agent) can be used during calibration, with the selected gaseous contrast agent being substituted after calibration is completed, thereby avoiding waste of contrast agent. Optionally, the memory 150 of the system 10 can have a database of system parameters associated with particular subjects (i.e., gas species, tidal volumes, flow ratios, etc.) such that, following initial calibration for a subject, the system (and processor 110) can access stored parameters, and imaging can commence without the need for additional calibration.

In imaging procedures, following delivery of the gas mixture to the subject, the subject can commit a voluntary breath-hold during which images are acquired. After the subject exhales, the gas delivery sequence can be repeated for subsequent breaths.

In exemplary aspects, the system 10 can be employed in a method for quantitative fractional ventilation in the subject. In these aspects, a series of identical gas mixture volumes can be delivered to the delivery tube. Following delivery of each gas mixture to the subject, the processor 110 can be configured to activate the imaging device 90 at the same point in the respiratory cycle of the subject or at the same point within a sequence of breaths of the subject.

It is contemplated that the disclosed system can allow the subject to maintain a respiratory pattern very similar to normal breathing, with only the addition of a short breath-hold (approximately one second for a set of images covering the entire lung, especially when combined with image acceleration).

It is contemplated that accelerated specific ventilation and/or undersampling techniques can be applied to a system comprising an MRI machine to permit faster image acquisition of multiple lung slices per breath of the subject while continuing to allow the subject to breathe at a substantially normal rate. It is further contemplated that the shorter acquisition time can reduce the signal attenuation associated with oxygen gas, which typically builds up during slower breathing. It is still further contemplated that, due to the smaller number of radiofrequency (RF) pulses that are applied, these techniques can reduce the irreversible depolarization of respiratory gas.

It is contemplated that the disclosed systems and methods can permit direct visualization of respiratory gas distribution in the airways of a subject while providing desired temporal resolution, spatial resolution, and safety features. It is further contemplated that the described system 10, when coupled with specific ventilation methods, can provide for shorter imaging times, thereby limiting exposure to radioactivity or ionizing radiation. It is still further contemplated that the multi-breath ventilation functionality of the system can provide richer information content compared to the more ubiquitous single-breath ventilation scans. It is still further contemplated that the described systems and methods can permit more accurate and earlier diagnosis of respiratory diseases, as well as assessment of the efficacy of therapeutics with better sensitivity to localized changes. It is still further contemplated that the described system 10, when coupled with specific ventilation methods, is objectively comparable among different populations and over any period of time.

Exemplary applications of the disclosed system include: performing oxygen tension imaging and/or specific ventilation imaging, which require strict control of the pattern and concentration of gaseous contrast agent delivery. It is contemplated that pulmonary/radiology research centers can use the disclosed systems and methods for investigational use of HP gas MRI and/or to perform sponsored respiratory therapeutic studies. It is further contemplated that the disclosed systems and methods can be used to perform multi-site imaging HP gas MRI trials, where dose standardization, repeatability of ventilation volume and gas concentration, and quality control and assurance are required. Exemplary studies in which the disclosed system can be used include any multi-site respiratory therapeutic imaging study or disease progression study that utilizes HP gas MRI as a radiologic biomarker.

In additional exemplary applications, it is contemplated that the disclosed system 10 can be used in a multi-breath $pO_2$, imaging protocol as further described herein. It is further contemplated that the disclosed system 10 can be used to perform oxygen tension imaging as further described herein. In still further exemplary applications, it is contemplated that the disclosed system 10 can be used in a method for simultaneously imaging specific ventilation and pulmonary oxygen tension using a multiple-breath HP gas MRI protocol as further described herein.

In exemplary aspects, it is contemplated that the processor 110 can be configured to perform one or more of the image processing steps set forth in the following examples.

EXAMPLES

The following examples are put forth so as to provide those of ordinary skill in the art with a complete disclosure and description of how the compounds, compositions, articles, devices and/or methods claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

Example One

A prototype of the disclosed system was built and tested with HP $^3$He in a 1.5-T Siemens Sonata MRI scanner. The prototype used custom-made MRI-compatible differential pressure pneumotachometers that independently report the flow rate of each gas component and trigger the pneumatic valves and the MRI scanner when the target volume is reached. The subject then committed a voluntary breath-hold during which images were acquired, exhaled freely, and the sequence was repeated as desired. Flow calibration was performed using the effective molecular weight of the gas mixture in each bag and also experimentally by withdrawing a known quantity of gas from the bags and comparing the volume to the time integral of the flow sums. Finally, the calibration coefficients were tested and fine-tuned with the subject inhaling the total volume of the desired gas mixture (with $^3$He replaced by $^4$He) before starting the MRI scan. It is contemplated that the calibration step can eventually be eliminated once the system is "trained" by collecting enough data points over time to form a database for various gas species and tidal volumes from different subjects. The system allowed for real-time fine-tuning of flow ratios by optionally placing the reservoir bags in chambers filled with an inert gas where their internal pressure was continuously adjusted (within 0-10 cm $H_2O$) to compensate for the nonlinear behavior of shrinking bags, different line resistance, and/or drift in system performance over time.

Figure 4:
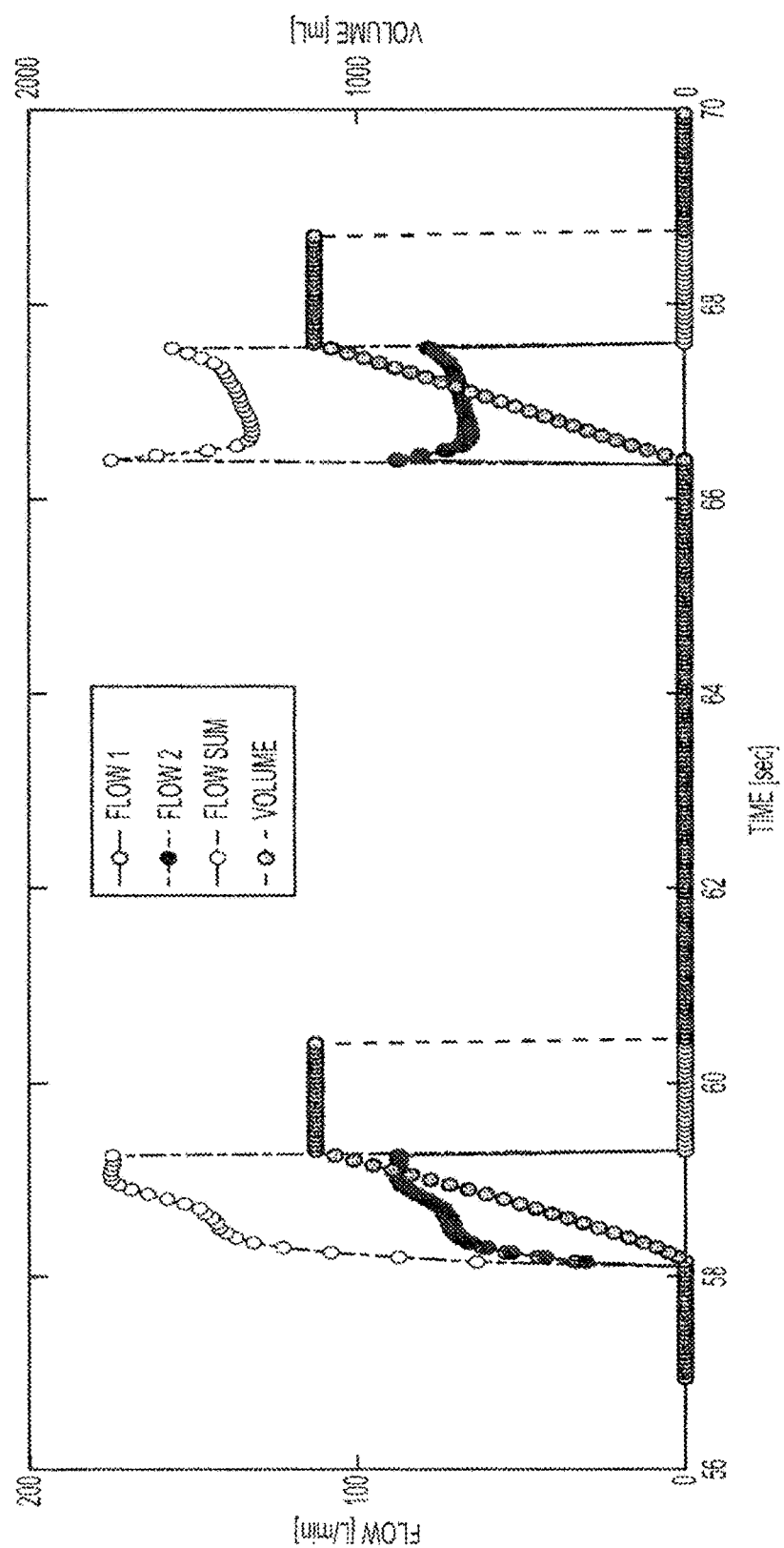
FIG. 4 depicts an exemplary real-time readout of gas flow from two channels over the course of two respiratory cycles of a subject.

The pressure differences between pressure transducer 76 and pressure transducer 48 and between pressure transducer 71 and pressure transducer 48 were used to estimate the real-time flow of the two channels respectively. The pressure difference between pressure transducer 46 and pressure transducer 48 was used to sense the presence of flow and to threshold the baseline noise. FIG. 4 shows a representative real-time readout of flow from both channels and the computed inhaled volume over two respiratory cycles. Coronal lung images of a healthy volunteers (25-yrs old male) were acquired during 5 back-to-back breaths ($V_T$=700 mL, I:E~3:4, ~8 BPM) from two separate bags ($^3$He—$N_2$ and $O_2$—$N_2$, 2.1 L each, for a total of $^3$He:$N_2$:$O_2 \approx 25$:55:20).

The volume delivery repeatability was experimentally evaluated at better than ±50 mL per breath (5-7% for an adult breath size). The performance was fairly sensitive to the gas mixture composition. In order to avoid the need to recalibrate the system before every single experiment, it was beneficial to maintain a similar gas ratio in different bags (e.g. $O_2$ in bag 1, and $^3$He:$N_2$=1:1 in bag 2) for different studies. Otherwise, an initial calibration coefficient can be assumed based on the molecular weight of the gas species and then fine-tuned by having patients inhale a few single breaths of the desired gas mixture at the prescribed tidal volume. The system monitored the inspiration flow only, given the focus on inspiratory ventilation imaging. However, it is contemplated that the utility of the system can be easily extended to monitor expiratory flow by incorporating an additional pneumotachometer on the exhale path. It is contemplated that such a system can be used for end-expiratory lung MRI. However, it is further contemplated that such a system would expose several more components of the system to expired gas and therefore necessitate disposal of those components after each study.

The disclosed system included two sets of components: MRI-compatible components and Non-MRI-compatible components. The MRI-compatible components included the pneumotachometers, tubing, pneumatic valves, pressure transducers, and gas containers, plus an optional remote display monitor for the study assistant. It is essential to place these components as close as possible to the MRI scanner in order to minimize the respiratory dead space and the depolarization of HP gas. The Non-MRI-compatible components included the controller computer, pressure transducer interface modules, and compressed air source. These components can be positioned outside of the MRI scanner room.

The computing power requirement of the system was fairly modest. The four pressure transducer signals were sampled real-time at a frequency of ~50 Hz and integrated with respect to time to yield volume history. The pneumatic valves were controlled using a simple digital control module. A single USB data acquisition (DAQ) card was used to perform the real-time data acquisition and control tasks in conjunction with a custom-made user interface program in the LabView environment.

Currently known devices are incapable of meeting the combined set of design criteria specified herein, which are essential for performing controlled HP gas MRI protocols similar to those described in further herein. Moreover, no known device captures the combined requirements set forth herein for delivery of gaseous or aerosolized contrast agents for pulmonary imaging (such as the radioactive gas $^{133}$Xe or rare isotope $^{17}$O). Some of the outlined criteria are strictly unforgiving, namely: MRI-compatibility, low ventilation dead space, non-depolarizing materials, discrete regulation of breath under spontaneous breathing, and real-time concentration and volume control.

Some known devices based on peristaltic pumps (such as those designed for $^{17}$O MRI) introduce a relatively large dead space relative to the total HP gas mixture available per imaging session. Since these devices need to be kept far away from the MRI scanner due to its peristaltic pumps and other metallic components, there is a need for several feet of gas transport tubing (with a minimum ~1" ID), which can add up to several hundred mL, and up to 1-2 L of ventilation dead space, compared to 1-2 L of HP gas diluted in the buffer gas. In contrast, the pneumatic valves of the disclosed system are mounted very close to the MRI scanner, almost immediately before the respirator valve connected to the mouthpiece and/or facemask. Additionally, it is contemplated that the materials used in the peristaltic device (including metal and high carbon plastics) can depolarize the HP gas upon contact with the HP gas.

In the field of HP gas MRI, the common practice over the past decade has been to use specialty low permeability dose bags (e.g. Tedlar or Altef) to administer the HP gas to the subject. However, as described above, this bolus approach is only suitable for simple single-breath MRI scans and does not meet the requirements for more sophisticated imaging protocols requiring multiple breaths or accurate gas concentration. In addition to enabling specific MRI protocols, it is contemplated that the disclosed system can assist in improving measurement repeatability and standardizing HP gas MRI protocols across different sites and on multiple days; it also can eliminate problems associated with manual delivery of HP gas to voluntarily breathing subjects. During oxygen-weighted MRI in human subjects, it is contemplated that one of the factors contributing to measurement accuracy and repeatability is a robust and simultaneous delivery of $^3$He:$N_2$ and $O_2$ mixtures to the subjects.

Example Two

An exemplary method for specific ventilation imaging in consciously breathing human subjects using HP gas MRI was examined. A semi-automated HP gas mixing and delivery device and system as disclosed herein used real-time monitoring and control of the two respiratory gas components (i.e. HP gas and oxygen) while maintaining $FiO_2$ and $V_T$ at desired levels and simultaneously triggering an MRI scanner to acquire the images at the proper time during a multi-breath sequence. It is contemplated that use of the disclosed system in this manner Accelerated Ventilation Imaging The use of image acceleration using undersampled MRI (e.g. parallel MRI or radial MRI) was shown to improve measurement accuracy of quantitative HP gas SV imaging in the human subjects.

Imaging acceleration through undersampling provided multiple benefits in this context. First, it permitted fast image acquisition of several lung slices per breath while allowing the subject to breathe at a nearly normal rate. Further, a shorter acquisition time reduced the oxygen-induced signal attenuation, which can be a significant factor when breathing slower. Additionally, the irreversible depolarization of respiratory gas was reduced by applying a smaller number of RF pulses. These benefits ultimately assisted in better decoding of the SV information from the HP gas signal buildup in the airways.

Stage of Development

Accelerated Specific Ventilation MRI

In order to assess the effect of image acceleration on accuracy of SV imaging and to determine the optimal acceleration parameters a series of simulations and animal experiments were performed. Briefly, a single voxel model was used to assess the fundamental effects of undersampling on the accuracy and optimality of flip angle and SV estimation in the presence of noise. Additionally the effect of image acceleration on SV error was assessed on a series of previously acquired lung images reconstructed at different spatial resolutions. Phantom studies were performed to experimentally validate the flip angle estimation accuracy as a function of number of images and acceleration. Finally, the utility of accelerated SV imaging was demonstrated on five mechanically ventilated pigs using a representative set of parameters comparable to simulation results.

Specific Ventilation Imaging—Implementation in Humans

Mixtures of HP $^3$He—$N_2$ and $O_2$—$N_2$ were prepared in two separate bags (2.1 L each, $^3$He:$N_2$:$O_2 \approx 25$:55:20) administered over 6 breaths (I:E=3:4, ~10 BPM), while monitoring $SpO_2$, HR, BP and RR. MRI was performed in a 1.5-T Sonata MRI scanner (Siemens Healthcare) using an 8-channel chest coil (Stark Contrast) and GRAPPA ~2× acceleration (5×22-mm coronal slices, 4-mm spacing, ~6×6 mm$^2$ spatial resolution, FOV=40×30 cm$^2$, α=~5°, TR/TE=3.6/3.3). Two volunteers underwent the feasibility studies: a 25-yr old healthy male ($V_T$=700, BMI=19.6), and a 69-yr old active smoker (60 pack-yrs, $V_T$=750 mL, BMI=25.0, $FEV_1$/FVC=0.61, $FEV_1$=62% pred.), suspected as a stage II COPD.

Coronal $^3$He density images from the lungs of the healthy and smoker subjects were acquired over the course of a six-breath breathing sequence. The SNR in the last image (corresponding to the sixth breath) ranged over 50-70 given the continuous administration of oxygen during the study. It is evident that apart from the overall signal intensity, the two image sets are qualitatively the same for the healthy subject. The first important observation—and possibly somewhat different from single-breath ventilation images reported before—is that the distribution of gas in the smoker is drastically different between the first and last breath.

Numerous regions in the smoker's lung exhibited nearly no signal in the first image (corresponding to the first breath), while the respiratory gas eventually found its way into the lungs after several breaths, indicating a heterogeneous distribution time constant and likely an air trapped region. On the contrary, there were a number of areas (mostly peripheral and apical) in the lung that, even after several breaths, remained inaccessible by the respiratory gas, likely indicating a pulmonary shunt or severe obstruction. Quantitative maps of SV were overlaid on corresponding $^1$H images of the thorax. Specific ventilation distribution was fairly uniform in the parenchyma of the healthy subject's lung. High SV values were observed in the trachea and major bronchi as expected. An area near the heart showed an artificially high value, likely due to motion artifacts. The SV distribution was a lot more heterogeneous in the smoker's lung, as suspected. An interesting observation is that regions which were in the proximity of gross ventilation defects (as judged from spin density images) exhibited an unusually high SV value. At the same time, the regions which slowly became visible in transition from the first to last breath, showed a proportionally low SV value. Without being bound by any particular theory, it is contemplated that this observation is likely due to the transport of gas between the well-ventilated and poorly-ventilated regions, and the fact that this distribution takes place at different time constants among various regions in the lung, especially those afflicted by airway obstruction, air trapping, or pulmonary shunt.

Thus, it is contemplated that HP gas MRI provides a viable imaging platform for direct visualization of respiratory gas distribution in the airways with desired temporal and spatial resolution, as well as an attractive safety profile. It is further contemplated that HP gas SV MRI can eliminate the majority of the concerns associated with imaging resolution, scan time, exposure to radioactivity or ionizing radiation present in known imaging modalities. As described in herein, the multi-breath ventilation maneuver can provide a much richer information content compared to the more ubiquitous single-breath ventilation scans which may be of clinical utility for more accurate and earlier diagnosis of respiratory diseases, as well as to assess efficacy of therapeutics with better sensitivity to localized changes. Moreover, SV is a fairly established quantitative metric of ventilation distribution, which is objectively comparable among different populations and over a period of time.

Example Three

In another experimental example, a hyperpolarized (HP) gas MRI technique was implemented to measure whole-lung regional fractional ventilation (r) in Yorkshire pigs (n=5) through the use of a system as disclosed herein.

Theory

Fractional Ventilation Model

The fractional ventilation in acinar airways ($r_A$) can be defined as the ratio of the amount of fresh gas added to a volume element in the lung during inspiration ($V_f$) to the total end-inspiratory gas space of that volume element ($V_t$) (comprising $V_f$ and the residual volume $V_r$):

$$r_A = \frac{V_f}{V_t} = \frac{V_f}{V_f + V_r}$$

A voxel's end-inspiratory gas content under breath-hold pressure can be assumed to be divided between $r_A$, consisting of the delivered fresh gas, and $1-r_A$, representing the residual capacity of the volume element. $r_A=0$ indicates no gas replacement (completely occluded airways) and $r_A=1$ indicates complete gas replacement with each breath (conductive airways).

Over a series of breaths, the net magnetization of HP gas can increase at a faster rate in normal regions than in poorly ventilated regions. In theory, after an infinite number of $^3$He breaths, the available magnetization in each region of the lung can converge to a steady-state value specific to each region. The steady-state value can be proportional to the total airway volume present in the respective region of interest (ROI). The resulting magnetization after inhalation of an HP gas breath can be a function of the magnetization of the fraction $r_A$ of the fresh gas and of the fraction $1-r_A$ of the residual gas. During the same time interval between the two breaths, the polarization of HP gas can decay according to the partial pressure of oxygen (PO$_2$) present in the airways (P$_A$O$_2$ in the alveoli). At normal body temperature, the relaxation time constant for $^3$He can be given by $\xi/PO_2$, with $\xi \approx 2.6$ bar Serial Ventilation Sequence A series of back-to-back HP gas breaths with images acquired during short end-inspiratory breath-holds (referred to as a "serial ventilation sequence") can be used to measure lung fractional ventilation. Each ROI can be considered as a single-compartment inflatable volume element and can be assumed to have one port through which gas enters and leaves the volume element at end-inspiration and end-expiration, respectively. FIG. 5(a) shows a multislice serial ventilation sequence acquiring N time points to form a signal buildup curve in the airways. The time interval between two consecutive images acquired at the same time in the respiratory cycle is $\tau$.

The dead space volumes in the ventilation system can be divided into two main components: (i) the "dynamic" dead volume ($V_D$) containing the major conductive airways and the portion of the ventilator system after the respirator valve, including the endotracheal tube—$V_D$ can experience a bidirectional gas flow during respiration; and (ii) the "static" dead volume ($V_s$) containing parts of the ventilator system that carry the source gas towards the respirator valve's inlet, primarily containing a transmission line between the HP gas chamber and the respirator valve. $V_s$ can experience only a unidirectional flow from the source through the transmission line, which eventually fills up the dead space. The magnetization of the gas in each of the compartments is labeled according to FIG. 5(b): $M_A$ (acinar airways, including alveoli and small airways), $M_C$ (dynamic dead space), $M_T$ (static dead space), and $M_S$ (HP gas source reservoir).

The available magnetization in the airways at each step of the ventilation sequence can be recursively expressed as a function of the fresh and residual gas from the previous step:

$$M_A(j) = r \cdot M_T(j-1) + (1-r) \cdot 9 M_A(j-1) \cdot \exp\left[N_{PE}\ln(\cos\alpha) - \tau \cdot \frac{P_A O_2}{\xi}\right],$$

$$M_A(0) = 0$$

where $r = r_A \cdot (1 - V_D/V_T)$ is the apparent fractional ventilation. It was assumed that the entrance of HP gas from the source pushed the same volume of gas as that of the tidal volume ($V_T$) out of the static dead volume. Therefore, for large species with $V_T/V_S > 1$, this results in:

$$M_T(j) = M_S, \quad M_T(0) = \left[1 - \left(\frac{V_T}{V_S}\right)^{-1}\right] M_S$$

For the purposes of these simulations and this sensitivity analysis, the signal intensity was approximated in a single imaging pixel subject to an RF pulse train with a fixed $\alpha$ and $N_{PE}$ encoding lines as:

$$S_A(j) = \eta \cdot \left[M_A(j) \cdot \frac{\sin\alpha}{N_{PE}} \sum_{i=0}^{N_{PE}-1} \cos^i\alpha\right]$$

where $\eta$ is a proper scaling factor.

The oxygen-induced depolarization rate of HP $^3$He, which is the second exponent term in the second equation (above), is a function of the oxygen tension in the airways. By neglecting the uptake of oxygen into the blood during each breath, it is contemplated that the partial pressure of oxygen in the airways (P$_A$) can be recursively expressed, at the beginning of each $^3$He breath, as a function of the oxygen concentration of the freshly arrived gas (P$_S$) and of the residual gas in the airways from the previous breath:

$P_A(j) = r_A \cdot P_S + (1-r_A) \cdot P_A(j-1), P_A(0) = P_A O_2 = 140$ mbar

Methods

Model Sensitivity and Optimization

The signal buildup in acinar airways was simulated using the above equations for a single imaging pixel. The standard deviation of the estimated parameters ($\alpha$ and r) was calculated as a measure of the sensitivity of the respective parameter with respect to noise and other measurement uncertainties. The model was constructed using a priori values for parameters over a range of $\Delta r$ and $\alpha$ values, as shown in Table 1. Model sensitivity was compared in large versus small animals as a function of noise, oxygen and the number of flip angle images (n). Specifically, the effects were simulated for pigs (with three slices per breath) and rats (one slice per breath). All sensitivity analyses combined $\alpha$ and r error effects in order to provide a more realistic measure of their coupled nature. If, at any given trial, the $\alpha$ estimation failed to converge, a random value was selected in the range of the nominal flip angle ($\alpha_{nominal} \pm 2°$), and r was computed accordingly.

TABLE 1

| Parameter | Description | Units | Rat | Pig |
|---|---|---|---|---|
| NS | Number of slices | — | 1 | 3 |
| MS | Matrix size | — | 64 | 48 |
| TR | Repetition time | ms | 7 | 7 |
| PAD | Pre-acquisition delay | ms | 500 | 500 |
| N | Number of ventilation images | — | 10 | 7 |
| BR | Breathing rate | breaths/min | 60 | 16 |
| FRC | Functional residual capacity | mL | 4 | 800 |
| $V_D$ | Dynamic dead space | mL | 0.5 | 15 |
| $V_S$ | Static dead space | mL | 3.5 | 15 |
| I:E | Inspiratory-to-expiratory ratio | — | 1:2 | |
| $V_T$ | Tidal volume | mL | FRC · r/(1 − r) | |
| $P_S$ | Source oxygen concentration | mbar | 140 | |
| r | Fractional ventilation | — | 0.1-0.4 | |
| $P_AO_2$ | Alveolar partial pressure of oxygen | mbar | 0-200 | |
| α | Flip angle | deg | 3-8 | |
| SNR | Signal-to-noise ratio in image 2 | — | 5-60 | |

The effect of oxygen was assessed by assuming a nominal $P_AO_2$ value, the signal buildup was computed accordingly and the noise-free model was used to estimate α and r values with two common assumptions: $P_AO_2$=0 mbar for α estimation and $P_AO_2$=140 mbar for r estimation. For noise analysis, the estimation accuracy was evaluated with respect to SNR of the second image in the series with magnetization $$M_A(2)=r \cdot r_S \cdot M_S[r_S<1, \text{given that } M_A(1)=0 \text{ for } M_T(0)=0]$$

Normally distributed noise with zero mean and a proper variance was added to the second image to yield the desired SNR value. The same noise variance was then randomly added to all images in the sequence. Each noise level was simulated 1000 times. The standard deviation of successful trials corrected for sample size was then reported.

The coupled sensitivity of r and α was simultaneously assessed for a range of r and n (number of images) in the presence of noise. The optimal α value was then determined based on the minimization of the r error. Comparisons were normalized with respect to the SNR as a function of α and $N_{PE}$ values. The available polarization was determined by fractional ventilation magnetization buildup. An arbitrary SNR value was assigned to a nominal set of parameters from which the corresponding noise variance was derived and added to the signal amplitude for all other cases, as determined for a single pixel as described above.

Animal Preparation and Mechanical Ventilation

The multislice serial ventilation imaging technique was implemented on five healthy Yorkshire pigs. Pigs were anesthetized with intravenous administration of ketamine and xylazine, intubated with a 6.5 mm cuffed endotracheal tube (Teleflex Medical-Rusch, Research Triangle Park, N.C., USA) and placed inside the MRI scanner in a supine position. A high-precision, MRI-compatible mechanical ventilator capable of mixing up to three different types of gas at different ratios. The ventilator gas-handling unit was comprised entirely of pneumatic and nonmagnetic delivery valves, placed in proximity to the RF imaging coil, as close as possible to the animal in order to minimize ventilator dead spaces. The HP gas was stored in a 2 L Tedlar plastic bag (Jensen Inert Products, Coral Springs, Fla., USA) and mounted inside a hard plastic chamber, which was pressurized up to 8-10 psi with nitrogen (regulated by a ventilator) for controlled delivery to the animal. A secondary chamber was connected in series to the main chamber in order to reduce the fluctuation of internal pressure as the HP gas was depleted during the imaging process. For the pig valve setup, $V_D$ was approximately 15 mL (between the $^3$He chamber and the respirator valve). For normal breathing, animals were ventilated with air at $V_T$=7-9 mL/kg, 14-18 breaths per minute (BPM) and an inspiratory-to-expiratory ratio (I:E)=1:2. Details of the variation in ventilator parameters are provided in Table 2.

TABLE 2

| Pig | Weight (kg) | Respiratory rate (breaths/min) | $V_T$ (mL) | n | Peak SNR | r Ventral slice | Middle slice | Dorsal slice | Overall r |
|---|---|---|---|---|---|---|---|---|---|
| 1 | 20.5 | 14 | 150 | 2 | 45 | 0.27 ± 0.15 | 0.38 ± 0.16 | 0.40 ± 0.15 | 0.36 ± 0.16 |
| 2 | 25.0 | 16 | 200 | 5 | 42 | 0.15 ± 0.13 | 0.29 ± 0.16 | 0.38 ± 0.14 | 0.30 ± 0.17 |
| 3 | 22.0 | 16 | 200 | 5 | 54 | 0.35 ± 0.14 | 0.40 ± 0.12 | 0.45 ± 0.13 | 0.41 ± 0.13 |
| 4 | 23.0 | 16 | 200 | 5 | 57 | 0.17 ± 0.13 | 0.26 ± 0.17 | 0.34 ± 0.15 | 0.27 ± 0.17 |
| 5 | 26.0 | 18 | 200 | 5 | 47 | 0.32 ± 0.15 | 0.39 ± 0.18 | 0.43 ± 0.15 | 0.38 ± 0.17 |
|   |      |    |     |   |    | 0.25 ± 0.09 | 0.34 ± 0.06 | 0.40 ± 0.04 | 0.34 ± 0.06 | r > 0.9 masked.

Imaging Techniques

The imaging helium gas (Spectra Gases, Branchburg, N.J., USA) had a nominal concentration of 99.19% $^3$He and 0.81% $N_2$. This mixture was hyperpolarized through spin exchange collisions with optically pumped rubidium atoms, using a commercial polarizer. All imaging experiments were performed in a whole-body 1.5-T MRI system using a flexible eight-channel (2×4 phased array) chest coil tuned to the nominal $^3$He resonance frequency of 48.48 MHz. Three $^3$He coronal images were acquired using a two-dimensional multislice gradient echo pulse sequence at a planar resolution of 3.75×3.75 mm$^2$ employing the following parameters: field of view (FOV), 24×18 cm$^2$; slice thickness, 30 mm; slice spacing, 6 mm; α=3-4°; matrix size, 64×48 pixels; TR=7.0 ms; TR=3.3 ms. Proton images were acquired in a similar manner.

Ventilation images were acquired using the multislice serial ventilation sequence (FIG. 5(a)) during an approximately 1.5-s-end-inspiratory breath-hold following each HP $^3$He breath. A 500-ms end-inspiratory pre-acquisition delay was incorporated to allow the lung tissue to reach a steady-state volume prior to acquiring the images. For imaging, the concentration of the administered HP gas was controlled with the ventilator at $^3$He:$N_2$:$O_2$ of approximately 2:2:1. A total amount of 1.0 L of HP gas mixture was prepared for each study by mixing 500 mL of $^3$He and 400-500 mL of $N_2$ in a Tedlar bag inside the gas delivery chamber and placed inside the bore of the MRI scanner. The mixture was then delivered to the intubated animal using the MR-compatible ventilator. Each measure of fractional ventilation was completed in approximately 2.0 minutes.

The regional distribution of the flip angle α was measured by acquiring a series of back-to-back images (n=5, unless otherwise stated) with no interscan time and imaging parameters identical to those of the ventilation imaging sequence. The flip angle images were acquired at the end of the ventilation sequence while the last breath was held for approximately 5 s. This ensured an identical lung position and inflation level to those in ventilation images. Each slice was imaged five times, as shown in FIG. 5(a). The RF-induced polarization decay of HP $^3$He was then calculated from:

$$M_A(j) = M_A(N) \cdot \exp[j \cdot N_{PE} \cdot (\ln(\cos\alpha) - TR \cdot P_AO_2/\xi)]$$

Data analysis was performed using custom MATLAB programs.

Results

Sensitivity Analysis and Optimization

FIG. 5(c) shows a representative combined r and α measurement experiment with noise added to the nominal signal with parameters typical of a pig study (Table 1). Also shown is the best fit to the noisy data. The plateau signal of the ventilation sequence (N=7) serves as the initial signal for the flip angle measurement sequence. In the absence of noise, the systematic error in r estimation as a function of oxygen concentration misassumption in the airways is shown in FIG. 6. The actual $P_AO_2$ value is shown on the abscissa versus the nominal 140 mbar assumed everywhere. The $PO_2$-induced error in pigs (NS=3 per breath) was substantially larger than in rats (NS=1 per breath), over r=0.2-0.4. The error bars represent the Δr variation as a function of $N_{PE}$=24-64. Assuming a perfect knowledge of α, the error in r is shown in FIG. 7 as a function of SNR in the second image of the ventilation sequence, using N=10 breaths. The r estimation accuracy in pigs was up to three times more sensitive to noise than it was in rats.

A representative set of α sensitivity assessments as a function of the number of images (n) is shown in FIG. 8 for a single voxel with $N_{PE}$=48 and SNR=22. For small flip angles (α approximately 3°), the estimation accuracy improves almost uniformly with larger n values. Larger flip angles (α approximately 6°), however, lead to a local minimum in the estimation error as a function of the number of images, beyond which the acquisition of more images adversely affects the α estimation accuracy. The estimation error in r as a function of the applied α value was used to determine the optimal flip angle over a range of r=0.1-0.3 for the same imaging pixel, as shown in FIG. 9 (using $N_{PE}$=48 and n=4). The optimal neighborhood of α becomes narrower for smaller r values as a result of a slower signal buildup in the airways. The variation of Δr versus α was fitted to a second-order function in order to assist in estimating the optimal flip angle, $\alpha_{opt}$=5.0-6.0°, for the respective range of r values.

Measurements of the Fractional Ventilation in Pig Lungs

Measurements of fractional ventilation were performed using the multislice r-α imaging technique in all animals over three coronal slices. The flip angle maps were measured using n=5 images during the tail-end breath-hold of the ventilation sequence. The mean r values for the entire group were 0.27±0.09, 0.35±0.06, and 0.40±0.04 for the ventral, middle, and dorsal slices, respectively (excluding conductive airways by masking r>0.9 voxels). The gravitational dependence of the ventilation distribution (a positive ventral-dorsal gradient) was present in all measurements.

Example Four

The utility of undersampled acceleration in multi-breath fractional ventilation (r) imaging was investigated. A simple single voxel model was used to assess the fundamental effects of undersampling on the accuracy and optimality of flip angle and fractional ventilation estimation in the presence of noise. Additionally, the effect of image acceleration on r error was assessed on a series of previously acquired lung images reconstructed at different spatial resolutions. Phantom studies were performed to experimentally validate the flip angle estimation accuracy as a function of number of images and acceleration. Finally, the utility of accelerated ventilation imaging was demonstrated on five pigs using a representative set of parameters comparable to simulation results.

Two-Dimensional GRAPPA Image Reconstruction

Two key parameters of Generalized Auto-calibrating Partially Parallel Acquisition (GRAPPA) acquisition and image reconstruction are the number of auto-calibration lines (ACL, equal to the number of PE lines acquired from the central region of the k-space) and the acceleration ratio (AR, equal to the undersampling ratio outside of the ACL region). The effective acceleration factor is given by the ratio of reconstruction resolution along phase encode direction, $N_y$, to the number of RF pulses, $N_{PE}$=ACL+($N_y$-ACL)/AR. To assess the effect of GRAPPA image reconstruction of parallel undersampled data on r estimation accuracy, a representative 2D image of the middle slice of a pig lung was used as a priori equilibrium HP $^3$He magnetization, $M_0(x,y)$. The corresponding r(x,y) map, derived experimentally from the same pig study, was used as the matching a priori fractional ventilation map. Using a uniform distribution of α=5° and $P_AO_2$=140 mbar, a series of images were generated corresponding to a multi-slice fractional imaging maneuver using parameters typical to the experimental pig studies (Table 3). Accelerated acquisition was simulated over ACL=8-32 and AR=2-5, and for spatial resolution ranging from 48×48 trough 128×128. Cartesian k-space sampling was used to simulate the MR signal according to:

$$S_c(k_x, k_y) = \sum_{x=1}^{N_{PE}} \sum_{y=1}^{N_{PE}} M_A(x,y) \cdot B_c(x,y) \cdot \sin\alpha \cdot \cos^{k_x-1}\alpha \cdot \exp[-(k_x-1)TR \cdot P_AO_2/\xi] \cdot \exp[j2\pi(k_x+k_y)/N_{PE}],$$

where $B_c(x,y)$ represents the sensitivity profile for the c-th coil. Complex random noise was added to the k-space signal to obtain the desired SNR value. Parallel sampling was performed using a 1×4 phased array coil with an identical sinusoidal sensitivity profile. Final images were generated by summing the magnitude of four channels, which were then fit to the magnetization equation to yield maps for α and r.

TABLE 3

| Parameter | | Description | Units | Value |
|---|---|---|---|---|
| Pig Ventilation Simulations | NS | Number of slices | — | 3 |
| | MS | Matrix Size | — | 48 |
| | TR | Repetition time | ms | 7 |
| | PAD | Pre-acquisition delay | ms | 500 |
| | N | Numbers of ventilation images | — | 7 |
| | BR | Breathing rate | breaths/min | 16 |
| | FRC | Functional residual capacity | mL | 800 |
| | $V_D$ | Dynamic dead space | mL | 15 |

TABLE 3-continued

| | Parameter | Description | Units | Value |
|---|---|---|---|---|
| | $V_S$ | Static dead space | mL | 15 |
| | I:E | Inhale-to-exhale ratio | — | 1:2 |
| | $V_T$ | Tidal volume | mL | FRC • r/ (1 − r) |
| | $P_S$ | Source oxygen concentration | mbar | 140 |
| Sensitivity Analysis | r | Fractional ventilation | — | 0.1-0.5 |
| | $P_AO_2$ | Alveolar partial pressure of oxygen | mbar | 140 |
| | $N_{PE}$ | Number of phase encoding RF pulses | — | 16-64 |
| | α | Flip angle | deg | 3-8 |
| | SNR | Signal-to-noise ratio in image #2 | — | 5-60 |
| | n | Number of flip angle images | — | 2-10 |
| GRAPPA Analysis | MS | Matrix size | | 48-128 |
| | ACL | Number of auto-calibration lines | | 8-32 |
| | AR | Acceleration (undersampling) ratio | — | 2-5 |
| | C | Number of phased array coils | — | 4 |
| | N | Number of ventilation images | — | 6 |
| | n | Number of flip angle images | — | 4 |

Methods

Generally, the same methods of Example Six were followed. For accelerated imaging, the breath-hold was shorted to 1 second (rather than 1.5 seconds).

In the phantom studies, the phantom consisted of a 200 mL Tedlar plastic bag filled with a HP gas mixture of $^3$He:$N_2$ of approximately 1:4. Flip angle maps were measured in the phantom using both standard and accelerated acquisition methods by acquiring a series of 20 back-to-back projection images.

GRAPPA simulation results were evaluated in two different ways: (1) the RMS difference between the estimated and reference r maps, $$\hat{r} = \|\Delta r\|_2 = \|r - r_{ref}\|_2;$$

and (2) the correlation coefficient R for the voxel-by-voxel linear regression between the estimated and reference r maps. RMS r error was normalized with respect to the minimum error observed in the entire process, $$\|\Delta r\|_2 / \|\Delta r\|_{2,min}$$

A similar assessment was performed on the voxel-by-voxel correlation coefficient, R, between the estimated and a priori maps. Since in theory any given acceleration factor can be achieved using more than one combination of ACL and AR, the pair of parameters with the largest ACL value was used as the basis for comparison.

Results

Flip Angle Estimation and Number of RF Pulses

FIG. 11 shows the evolution of the estimated flip angle distribution in the bag phantom as a function of n. The initial SNR in both standard and accelerated measurements exceeded 100. The standard acquisition converged to an asymptotic mean α value of approximately 1.7° with as few as four images, whereas the accelerated acquisition required a minimum number of seven images to converge to the same quantity. The RMS error of α declined monotonically as a function of n corresponding to:

$$\|\Delta \alpha\|_2 \sim 0.3° \text{ for } n=5$$

using the standard acquisitions. The same error threshold was only reached by the accelerated acquisition at around n=10 images, in good agreement with single voxel simulation results (FIG. 10).

Flip angle maps were also measured in the middle coronal slice of five pig lungs using both standards and accelerated acquisition, separate from the ventilation sequence (external α maps), and correlated on a pixel-by-pixel basis (R=0.62-0.96). α measurements in pig #4 were done with the largest number of images in one breath-hold ($n_{ext}$=20), subsequently resulting in the highest correlation coefficient (R=0.96). As part of the fractional ventilation imaging study, a separate set of multi-slice flip angle maps was acquired at the end of the ventilation sequence (internal α maps), using $n_{int}$=5 (with the exception of pig #1), which were further used to compute the corresponding r maps as discussed in the following sections.

Coupled Dynamics of Flip Angle and Fractional Ventilation

The effect of α error was simultaneously assessed on r accuracy using the single voxel model. The diminished contribution of flip angle on fractional signal buildup by undersampling was expected to enhance the accuracy of r even at the price of a less accurate α. The r error as a function of the applied α value is shown in FIG. 12(a) over $N_{PE}$=24-64 (for the representative case of r=0.3 and n=4). The optimal flip angle ($\alpha_{opt}$) corresponds to the α value that minimizes r estimation error for any given number of RF pulses. The $\alpha_{opt}$ interval gets smaller for larger $N_{PE}$ values. Nevertheless, the optimal flip angle shows a highly linear behavior with respect to $N_{PE}$ (R=0.98-0.99 for r=0.2-0.4) and is confined to the range $\alpha_{opt}$ of approximately 5-7° for $N_{PE}$=24-64.

Effect of GRAPPA Accelerated Image Reconstruction

A series of reconstructed ventilation images of a representative pig lung were generated using the set of parameters shown in Table 3. The variation of RMS error and correlation coefficient of r maps for 64×64 resolution is plotted in FIG. 13 as a function of α and for the range of GRAPPA acceleration parameters ACL=8-32 and AR=2-5, where the effective acceleration factor is given by $N_y/N_{PE}$. A similar error pattern as a function of α is observed similar to the single voxel model (FIGS. 12(a) and (b)). Both $\|\Delta r\|_2/\|\Delta r\|_{2,min}$ and R reach a local optimal point as a function of α. Based on the RMS error, the r estimation accuracy improves with increased acceleration, compared to the baseline ($N_{PE}$=64 in this case). The error, however, reaches a global minimum (around $N_{PE}$=31, corresponding to an effective acceleration factor of approximately 2.1× in this case), beyond which the trend reverses. A similar behavior is observed in the correlation coefficient of r maps, where a global maximum is reached around 2.2×.

FIG. 14 summarizes the variation of r error as a function of acceleration factor for all simulated imaging resolutions: 48, 64, 96, and 128 matrix size, respectively. The optimal acceleration factor was fairly independent of imaging resolution: 2.0±0.1 (based on $\|\Delta r\|_2$) and 2.2±0.1 (based on R). The improvement in estimation accuracy, however, was progressively larger for higher resolutions: 39, 42, 49, and 51% (based on $\|\Delta r\|_2$) and 11, 14, 17, and 24% (based on R), corresponding to the four resolutions in the same order as above.

Measurements of Fractional Ventilation in Pigs

A summary of r measurements in the five healthy pigs is shown in Table 4 for each of the non-dependent, middle, and dependent slices. The two sets of measurements (standard and accelerated) correlated well (R=0.83-0.89).

TABLE 4

| Pig No. | Weight [kg] | Respiratory Rate [breaths/min] | $V_T$ [mL] | $n_{ex}$ | $n_{in}$ | R (r) | R(a) |
|---|---|---|---|---|---|---|---|
| 1 | 20.5 | 14 | 150 | 5 | 2 | 0.83 | 0.68 |
| 2 | 25.0 | 16 | 200 | 10 | 5 | 0.89 | 0.87 |
| 3 | 22.0 | 16 | 200 | 10 | 5 | 0.83 | 0.90 |
| 4 | 23.0 | 16 | 200 | 20 | 5 | 0.80 | 0.96 |
| 5 | 26.0 | 18 | 200 | 10 | 5 | 0.68 | 0.62 | r, Standard Acquisition

| Peak SNR | Nondependent Slice #1 | Intermediate Slice #2 | Dependent Slice #3 | Overall r | Gradient [cm$^{-1}$] |
|---|---|---|---|---|---|
| 45 | 0.27 ± 0.15 | 0.38 ± 0.16 | 0.40 ± 0.15 | 0.36 ± 0.17 | 0.018 |
| 42 | 0.15 ± 0.13 | 0.29 ± 0.16 | 0.38 ± 0.14 | 0.30 ± 0.17 | 0.032 |
| 54 | 0.35 ± 0.14 | 0.40 ± 0.12 | 0.45 ± 0.13 | 0.41 ± 0.13 | 0.014 |
| 57 | 0.17 ± 0.13 | 0.26 ± 0.17 | 0.34 ± 0.15 | 0.27 ± 0.17 | 0.024 |
| 47 | 0.32 ± 0.15 | 0.39 ± 0.18 | 0.43 ± 0.15 | 0.38 ± 0.17 | 0.015 |
|  | 0.25 ± 0.09 | 0.34 ± 0.06 | 0.40 ± 0.04 | 0.34 ± 0.06 | 0.021 ± 0.007 |

$P_{1-2} < 0.10$
$P_{2-3} < 0.15$ r, Accelerated Acquisition

| Peak SNR | Nondependent Slice #1 | Intermediate Slice #2 | Dependent Slice #3 | Overall r | Gradient [cm$^{-1}$] |
|---|---|---|---|---|---|
| 41 | 0.29 ± 0.16 | 0.38 ± 0.18 | 0.38 ± 0.16 | 0.36 ± 0.17 | 0.013 |
| 25 | 0.17 ± 0.15 | 0.30 ± 0.17 | 0.35 ± 0.15 | 0.29 ± 0.17 | 0.025 |
| 82 | 0.25 ± 0.16 | 0.35 ± 0.17 | 0.38 ± 0.16 | 0.33 ± 0.17 | 0.018 |
| 45 | 0.21 ± 0.13 | 0.31 ± 0.15 | 0.37 ± 0.15 | 0.31 ± 0.16 | 0.027 |
| 12 | 0.26 ± 0.13 | 0.34 ± 0.16 | 0.38 ± 0.18 | 0.33 ± 0.17 | 0.017 |
|  | 0.23 ± 0.05 | 0.34 ± 0.03 | 0.37 ± 0.02 | 0.32 ± 0.03 | 0.019 ± 0.005 |

$P_{1-2} < 0.005$
$P_{2-3} < 0.05$

The r distribution was qualitatively identical between each pair of measurements across the five pigs. No statistically significant difference between the two methods was observed: r=0.27±0.09, 0.35±0.06, 0.40±0.04 versus 0.23±0.05, 0.34±0.03, and 0.37±0.02 corresponding to the non-dependent, intermediate, and dependent slices, respectively. The intrasubject standard deviation of r by the accelerated method was approximately half that of the standard technique. Also reported were vertical fractional gradients in supine pig lungs: Δr/Δz=0.021±0.007 versus 0.019±0.005 [cm$^{-1}$] for the standard and accelerated techniques, respectively, showing no significant differences between the two methods.

Example Five

An improved method for imaging regional pulmonary oxygen tension using a multiple-breath HP gas MRI protocol was evaluated.

Overview

Oxygen-weighted hyperpolarized gas magnetic resonance imaging ($O_2$-weighted HP gas MRI) can be used as a diagnostic tool in detecting, staging and monitoring changes in lung function as a function of chronic exposure to cigarette smoke. Currently there is no clinically viable technique for real-time in vivo measurement of regional oxygen tension or gas exchange in human lungs. $O_2$-weighted HP gas MRI has never been investigated systematically to exploit its value either as a diagnostic tool in obstructive or interstitial lung diseases, or as a tool for monitoring disease progression or assessing response to new therapeutics. A multi-breath $O_2$-weighted imaging protocol is described below, enabled by using the HP gas delivery system disclosed herein, which, by addressing the limitation of the single-breath methods in use today, provides a more accurate way of mapping oxygen concentration in human lungs. Moreover, the results obtained in asymptomatic smokers advocate the utility of oxygen tension imaging as a biomarker in detecting and staging changes in the gas exchange of smoker lungs.

Oxygen Tension Imaging—Background

Similar to many other MRI contrast mechanisms, the signal from hyperpolarized gases can be manipulated using the RF pulse sequence parameters (such as timing and pulse angle) in order to exploit the richer information content beyond simply detecting the presence or concentration of the tracer molecule. Oxygen-weighted HP gas MRI can be used to measure the regional alveolar partial pressure of oxygen ($P_AO_2$). Oxygen molecules exhibit strong paramagnetic properties (due to the unpaired spins of its outermost two electrons), which in turn leads to a strong dipolar interaction with noble gas species and subsequently cause rapid depolarization (relaxation) of the HP gas. Hyperpolarized $^3$He for instance relaxes in presence of $O_2$ at a rate proportional to the partial pressure of oxygen according to:

$$S(t) = S_0 \exp[-P_A O_2 \cdot t/\xi]$$

where ξ≈2.6 [bar sec] under normal physiological conditions. Oxygen-weighted imaging was originally introduced by Weiler, et al., as described in U.S. Pat. No. 6,370,415, which is incorporated herein by reference in its entirety. Since then, various other implementations of the original idea have been proposed and optimized to acquire $P_AO_2$ maps using HP gas MRI in human lungs. The basic idea is to calculate a regional $P_AO_2$ value based on the decay rate of HP gas signal during a single breath-hold after inhaling a dose of HP $^3$He and $O_2$ mixture at the normoxic ratio of $^3$He:$O_2 \approx 79:21$.

Multi-Breath pO2-Imaging Protocol—Rationale

The conventional $p_AO_2$ imaging method is very sensitive to diaphragm motion, gas diffusion and any sort of abnormal flow during the required breath-hold, which can result in non-physiologic oxygen values. Slow fillings and collateral ventilations in COPD subjects have been reported during 15-25 sec breath-holds. These effects undermine the accuracy of the simplified assumption of gas being stationary during the breath-hold while being imaged, which is an essential assumption in the $p_AO_2$ estimation models currently in use. Preliminary studies of the multi-breath imaging protocol disclosed herein have shown that continuing to breathe the HP gas over a series of consecutive breaths— especially in patients with obstructive pulmonary disease— can gradually fill up some of the unventilated sections of the lung and lead to an overall improved MRI signal and a more uniform distribution of HP gas in the lung parenchyma. It is contemplated that this multi-breath $p_AO_2$ imaging method can mitigate some of the shortcomings outlined above. The more uniform HP gas distribution and the improved signal-to-noise ratio can result in a more accurate estimation of $p_AO_2$ values throughout the lung.

A sequence of HP $^3$He lung images was acquired in a representative COPD subject using the proposed multi-breath imaging protocol. The images showed generally more unventilated regions in the dependent parts of the lung, but the ventilated parts in this region filled up faster than the anterior slices. This example clearly demonstrated the advantage of the multi-breath HO gas administration protocol. Many regions of the lung were essentially inaccessible after only one breath. However, they filled up with HP gas after a few breaths and only truly defective regions remained unventilated, thereby providing a more accurate measure of ventilation defect. A more uniform distribution of HP gas also minimized the delayed ventilation and intra-compartmental diffusion of HP gas between well- and poorly-ventilated regions, which is detrimental to $p_AO_2$ estimation.

Multi-Breath pO2-Imaging Protocol—Method

The multi-breath $p_AO_2$ imaging method, shown in FIG. 15, is a natural extension of the specific ventilation protocols described further herein. Subjects breathe through a passive patient-driven gas delivery device (as disclosed herein), which maintains the gas mixture oxygen concentration (FiO2=21%) and tidal volume (12% TLC) over a series of consecutive breaths. After inhaling the last breath, the subject is instructed to hold her breath for 12 sec during which the image acquisition occurs. In the studies, subjects inhaled six identical breaths of normoxic mixtures of $^3$He:$N_2$:$O_2$ (1:3:1) before the long breath-hold.

Multi-Breath pO2-Imaging Protocol—Preliminary Results

To systematically investigate the effect of the multi-breath HP gas wash-in protocol on the computed $p_AO_2$ maps, the characteristics of both single- and multi-breath schemes were compared in the 12 subjects. The single-breath $p_AO_2$ maps showed adjacent regions of elevated and depressed $p_AO_2$ and a non-negligible number of negative and close-to-zero values as well as extremely high (non-physiological) values. Regardless of their physiological relevance, however, these features were indicative of anomaly and are therefore diagnostically useful. The improved quality of oxygen maps, as evidenced by substantially less non-physiological and negative values, was observed in the multi-breath technique. Hyperpolarized $^3$He transport during the breath-hold resulting from slow fillings, collateral ventilation and air trapping commonly present in damaged lungs skewed the $p_AO_2$ values toward higher or lower values depending on the dynamics of gas transport, as illustrated in FIG. 16.

The signal dynamics during the course of six breaths in a representative COPD subject were represented in spin-density maps. There were lung regions that remained unventilated even after the sixth breath. On the other hand, some of the unventilated regions in the early breaths were gradually filled through collateral pathways. The resulting quasi-steady-state gas concentration level alleviated the erroneous results of gas redistributions during the breath-hold more frequently observed in the case of single-breath $p_AO_2$ measurements.

Results from the experiments performed on four subjects from each group of COPD, nonsmokers and smokers suggested that the multi-breath regimen can significantly reduce the number of non-physiological $p_AO_2$ values compared to the conventional single-breath protocol. This improvement was most significant in the case of COPD subjects, followed by smokers.

Oxygen Tension Imaging—Advantages

The current standard of care for assessing lung function is PFT (or spirometry). This technique is more than a century old and is essentially based on force exhaling into a tube attached to a flow meter. The forced expiratory volume in one second normalized by forced vital capacity ($FEV_1$/FVC) is the current gold standard in assessment and staging of obstructive and restrictive lung diseases. It provides a global measure of lung function and is notoriously insensitive to early and localized pulmonary diseases. It is therefore also relatively insensitive to lung function recovery as a result of treatment or investigating new respiratory therapeutics. Moreover, spirometry results are highly dependent on patient cooperation and effort, which has adversely affected its reproducibility in the past for follow-up screening.

Currently, there is no practical way of directly measuring the distribution of oxygen tension or alveolar gas exchange in pulmonary airways. The traditional nuclear medicine techniques using radionuclide scintigraphy and radioactive elements (e.g. $^{133}$Xe and $^{99m}$Tc-DTPA) have been able to provide a measure of ventilation-to-perfusion ratio (V/Q). These modalities are, however, being rapidly decommissioned in clinical practice due to their poor spatial resolution and their radioactivity.

Oxygen Tension Imaging—Clinical Diagnostic Applications

An ongoing clinical trial is investigating the utility of $O_2$-weighted HP gas MRI for early detection and monitoring progression of COPD induced by chronic cigarette smoke with a target sample size of 100 subjects. So far, $P_AO_2$ imaging has been performed on 20 healthy subjects, 40 asymptomatic smokers—as determined by standard Pulmonary Function Testing (PFT) criteria—and 6 COPD subject for comparison. Mean and dispersion of $P_AO_2$ over the entire lung of each subject were calculated and compared among the groups. All subjects also underwent the standard of care practice of PFT to compare their sensitivity to HP gas MRI, as well as to highlight any underlying correlations.

Whole-lung $p_AO_2$ distribution mean and standard deviation values for all subjects were tested for differences among the three groups using a one-way ANOVA (n=92). FIG. 17 shows the statistical comparison results (P-value<0.0001 represents an excellent biomarker). Among all the listed PFT parameters $FEV_1$/FVC and FEF 25%-75% can successfully differentiate a COPD subject from asymptomatic smokers (also evidenced by minimum overlap between boxplots for COPD subjects with other groups). Other PFT results with P-value<0.005 (except RV/TLC %) also represent good markers of COPD and widely in clinical use. However, the PFT tests are also known to lack sufficient sensitivity to early smoking-induced changes since they measure the inspiratory and expiratory global values and are blind to regional changes in lung function. This was evidenced by major overlap between smokers and nonsmokers in FIG. 17; the only PFT parameter showing a desirable P-value~0.0001 is $FEV_1/FVC$. Corrected DLCO (DLCO/VA) was also statistically able to distinguish the groups, albeit with a lower significance (P-value~0.0004).

The $p_AO_2$ maps acquired using $O_2$-weighted HP gas MRI, on the other hand, was shown to be very sensitive to both ventilation and perfusion changes in the three populations. FIG. 18, left panel, shows the box plots of average whole-lung $p_AO_2$ values in the three cohorts indicating that the mean $p_AO_2$ was not significantly different among the subjects. The standard deviation of $p_AO_2$, as a measure of oxygen distribution heterogeneity, was on the other hand the most sensitive marker in differentiating all three groups. The standard deviation of the measured $p_AO_2$ originated from a combination of different factors including regional oxygen level, gas flow, gas diffusion and probably different regional oxygen uptake rates. Therefore, $sp_AO_2$ cannot be simply thought of as the standard deviation of pure distribution of $p_AO_2$ in the lungs, but it certainly can be interpreted as a combination of all other abnormalities that can be imaged using the proposed $O_2$-weighted HP gas MRI. The sensitivity of $sp_AO_2$ in distinguishing the smokers from nonsmokers was much more significant than its $FEV_1/FVC$ counterpart or any other PFT parameter for that matter. This data advocates $O_2$-weighted MRI as a sensitive biomarker to detect early local changes in lung function due to chronic exposure to cigarette smoke which can otherwise go undetected with today's standard pulmonary medicine diagnostic tools, most notably the widely available pulmonary function tests (PFT).

Oxygen Tension Imaging—Commercial Uses

The two primary application areas of $P_AO_2$ imaging as a radiologic biomarker for pulmonary gas exchange are: (1) earlier and more accurate diagnosis of pulmonary diseases characterized by gas exchange deficiency, including obstructive (e.g. emphysema) and interstitial (e.g. cystic fibrosis) lung diseases—the current standard of care Pulmonary Function Test (PFT; more than a century old practice) is very insensitive to early and localized lung diseases; and (2) Assessment and monitoring of disease progression and response to therapy—essential for cost effective and successful clinical trials of new respiratory drugs and other interventions; several respiratory therapeutic trials have failed simply because they did not meet the PFT criteria due to insensitivity or miscorrelation to regional lung function although patients quality of life improved.

COPD refers to chronic bronchitis and emphysema, a pair of commonly co-existing diseases of the lungs in which the airways become narrowed. This leads to a limitation of the flow of air to and from the lungs causing shortness of breath. In clinical practice, COPD is defined by its characteristically low airflow on pulmonary function tests. In contrast to asthma, this limitation is poorly reversible and usually gets progressively worse over time.

Despite being largely preventable, COPD is a major cause of disability. It is the fourth leading cause of death in the United States and is now the most common form of chronic lung disease. More than 12 million people are currently diagnosed with COPD. COPD develops slowly and is COPD is typically diagnosed in middle-aged or older people; symptoms often worsen over time and can limit the ability of the affected individuals to perform routine activities. This disease results principally from inhalation of toxic substances, usually chemicals in tobacco smoke, which activate epithelial cells to produce inflammatory mediators that trigger chronic inflammation and progressively deteriorate pulmonary function.

The high morbidity and mortality rates for COPD highlight both the failure to identify at-risk patients early in the disease process and the lack of effective intervention and treatment. Conventional methods to diagnose emphysema however have proven to be generally insensitive to early changes in the lungs, and up to 30% of lung function can be already lost before changes are observable in PFT.

Non-invasive Imaging-based early diagnosis of lung diseases therefore is of key importance in enabling physicians to perform early diagnosis and timely intervention, which can directly result in improving the quality of life of patients and reducing the overall cost to the healthcare system. Moreover, any non-invasive methodology that has enough sensitivity to detect COPD at an early stage can potentially be used as a monitoring tool to assess the progression of disease and response to therapeutic interventions in patients. The ability to safely assess the disease evolution can assist physicians in titrating the therapy as necessary or change the treatment plan early on if desired outcome is not achieved. Such capability is also of great value to pharmaceutical industries for development and testing of new therapeutics for COPD.

Although this example provides evidence in detecting functional changes in lungs of smokers, it is contemplated that this indication can be extended to all other progressive lung diseases which affect alveolar gas exchange.

Example Six

Method for Simultaneous Imaging of Specific Ventilation and Pulmonary Oxygen Tension Using Multiple-Breath HP Gas MRI Protocol This section describes an exemplary method for imaging regional specific ventilation, alveolar partial pressure of oxygen ($p_AO_2$), oxygen uptake (R), and lung microstructure (ADC) in conscious human lungs using a compact multi-breath imaging protocol. This application is enabled by using the patient-driven HP gas delivery device/system described herein. These measurements were performed simultaneously in an iterative method developed to achieve a more accurate picture of regional lung function at the alveolar level. This imaging protocol allowed for effective regional assessment of different aspects of lung disease in a manner analogous to classical measurements of DLCO, CT % air trapping, CT % emphysema, and airway wall thickness (AWT).

An imaging protocol for hybrid acquisition of specific ventilation (SV), alveolar oxygen tension ($p_AO_2$), apparent diffusion coefficient (ADC) and oxygen uptake (R) was employed. The subject inhaled a total number of 7 breaths at the end of each a set of acquired images. The first 6 breath-holds were carried out consecutively, and were about 2 seconds in duration each. During each of the short end-inspiratory breath-holds, a slice-selective gradient-echo (GRE; or any other appropriate) MRI pulse sequence was used to acquire 6 coronal slices that spanned the entire lung volume. Imaging acceleration (multi-channel parallel imaging in this case) was effectively utilized to minimize the time required to image all lung slices The 6 consecutive images were used to calculate the specific ventilation map by fitting the signal intensity to a dynamic recursive model.

ation rate, and BR is the breathing rate. This technique imposed a voxel-wise oxygen mass balance relating specific ventilation (SV) to the oxygen uptake (R).

TABLE 5

| Subjects | Weight [lb] | Smoked [pck-yrs] | ADC [cm$^2$/s] | pO2 [Torr] | FV | R [Torr/s] |
|---|---|---|---|---|---|---|
| 1 | 151 | — | 0.25 ± 0.05 | 105.4 ± 21.0 | 0.30 ± 0.28 | 2.06 ± 1.39 |
| 2 | 182 | — | 0.20 ± 0.06 | 116.8 ± 19.9 | 0.37 ± 0.32 | 2.50 ± 1.59 |
| 3 | 232 | — | 0.20 ± 0.07 | 75.8 ± 20.2 | 0.29 ± 0.32 | 3.25 ± 1.11 |
| 4 | 110 | — | 0.16 ± 0.06 | 108.3 ± 18.5 | 0.36 ± 0.29 | 2.53 ± 1.27 |
| 1 | 199 | 15 | 0.22 ± 0.15 | 102.1 ± 27.1 | 0.39 ± 0.23 | 2.96 ± 1.41 |
| 2 | 153 | 22 | 0.19 ± 0.05 | 108.9 ± 22.8 | 0.40 ± 0.23 | 2.69 ± 0.88 |
| 3 | 117 | 24 | 0.23 ± 0.05 | 109.0 ± 25.1 | 0.39 ± 0.25 | 2.43 ± 0.80 |
| 4 | 181 | 32 | 0.20 ± 0.07 | 119.0 ± 34.5 | 0.32 ± 0.26 | 1.95 ± 0.75 |
| 5 | 184 | 35 | 0.23 ± 0.11 | 97.8 ± 32.0 | 0.45 ± 0.22 | 3.28 ± 1.34 |
| 6 | 135 | 36 | 0.22 ± 0.13 | 92.3 ± 28.5 | 0.37 ± 0.29 | 3.20 ± 0.82 |

Prior to the very last breath, the subject was instructed to hold her breath for an extended 12-second breath-hold, during which simultaneous $p_AO_2$-ADC images were acquired. At this point, the HP $^3$He signal is at its highest level, and uniformly distributed in the lung parenchyma. During this long breath hold, 5 images were acquired in the following order: two consecutive low-resolution GRE images, a 'slow' slice-selective GRE image, and two interleaved diffusion-weighted images, respectively. The parameters for the two low-resolution images were similar to the parameters for the first 6 images, but image acceleration was not used and the matrix size was a factor of 4 smaller (16×12 vs. 64×48). The two low-resolution images were used to reconstruct a flip angle α map. The flip angle map was required to reconstruct the $p_AO_2$ map to decouple the contribution of the radio frequency pulses from the oxygen-induced depolarization. This map was used with the slow GRE and non-diffusion-weighted images to construct the $p_AO_2$ map. The diffusion-weighted images were used to reconstruct the ADC map. Finally, the ventilation map and the $p_AO_2$ maps were used to calculate the oxygen uptake (R) map. The complete imaging protocol can be typically completed in ~1 min.

Since the estimation of each unknown parameter is intertwined with the value of all other parameters, all image sets were simultaneously analyzed iteratively to arrive at a self-consistent solution satisfying the following equations, in which $S_n$ refers to the signal intensity of a given voxel in the n-th image of that type:

$$\alpha = \arccos\left(\left(\frac{S_1}{S_0}\right)^{\frac{1}{n_{PE}}}\left(1 + P_AO_2 \times \frac{TR}{\xi}\right)\right)$$

$$P_AO_2 = \frac{\xi}{\Delta t}\ln\left(\frac{S_0(\cos\alpha)^{n_{PE}}}{S_1}\right) + \frac{R\Delta t}{2}$$

$$ADC = \frac{1}{b}\ln\left(\frac{S_0}{S_1}\right)$$

$$R = (FiO_2 - P_AO_2) \times \frac{SV}{BR}$$

$$S_n = S_{n-1}\exp\left(-\frac{P_AO_2}{\xi BR}\right)[1 - (SV)(\cos\alpha)^{n_{PE}} + S_\infty \times SV]$$

In the equations above, $S_n$ is the signal intensity of a given voxel in the n-th image, $n_{PE}$ is the number of imaging phase-encodes, $\xi = 1984$ Torr·sec is the $O_2$-induced relax- This technique was been implemented on 10 human subjects, including 4 healthy nonsmokers and 6 asymptomatic smokers. The results of this study are summarized in Table 5. A representative dataset was prepared for an asymptomatic smoker. Preliminary results support feasibility and practicality of conducting these imaging protocols in conscious subject without the need for intervention or operator coaching. This technique guaranteed administration of HP gas to the subject with a physiologically relevant fraction of oxygen and nitrogen throughout the entire imaging session. This method also allowed using the minimum amount of HP gas to conduct all the measurements (versus performing four separate measurements) while providing the highest signal intensity, which directly improves the measurement accuracy. Moreover all four derived parametric maps are essentially acquired at the same lung inflation volume which facilitates their co-registration for further comparison. Finally, it is contemplated that the presented algorithm is the first of its kind for practical measurement of pulmonary oxygen uptake rate map in human lungs using HP gas MRI. Oxygen uptake rate can be directly related to alveolar pulmonary gas exchange, which is arguable the single most important function of lungs.

Although several embodiments of the invention have been disclosed in the foregoing specification and following appendices, it is understood by those skilled in the art that many modifications and other embodiments of the invention will come to mind to which the invention pertains, having the benefit of the teaching presented in the foregoing description and associated drawings. It is thus understood that the invention is not limited to the specific embodiments disclosed hereinabove, and that many modifications and other embodiments are intended to be included within the scope of the appended claims. Moreover, although specific terms are employed herein, as well as in the claims which follow, they are used only in a generic and descriptive sense, and not for the purposes of limiting the described invention, nor the claims which follow.

What is claimed is:

1. A system for delivery of a gaseous contrast agent to the lungs of a subject, the system comprising:
    a first gas container defining an interior volume configured to contain said gaseous contrast agent, said first gas container having an outlet in fluid communication with said interior volume;
    a second gas container defining an interior volume configured to contain oxygen gas, said second gas container having an outlet in fluid communication with said interior volume;

a flow meter having an inlet and an outlet, said inlet of said flow meter being in fluid communication with said outlets of said first and second gas containers such that said flow meter receives a mixture of said gaseous contrast agent and said oxygen gas, said flow meter being configured to produce a first flow signal indicative of the flow rate of said gaseous contrast agent within the flow meter and a second flow signal indicative of the flow rate of said oxygen gas within the flow meter;

a delivery tube defining a central bore and having a first end and an opposed second end, said second end of said delivery tube being configured for coupling to the mouth of said subject;

a first flow control valve positioned between said outlet of said flow meter and said first end of said delivery tube, said flow control valve being positioned in fluid communication with said outlet of said flow meter and said first end of said delivery tube, said flow control valve being configured to provide selective fluid communication between said outlet of said flow meter and said first end of said delivery tube;

a first pressure valve positioned between said outlet of said first gas chamber and said inlet of said flow meter, said first pressure valve being positioned in fluid communication with said outlet of said first gas container and said inlet of said flow meter, said first pressure valve being configured to provide selective fluid communication between said outlet of said first gas container and said inlet of said flow meter;

a second pressure valve positioned between said outlet of said second gas container and said inlet of said flow meter, said second pressure valve being positioned in fluid communication with said outlet of said second gas container and said inlet of said flow meter, said second pressure valve being configured to provide selective fluid communication between said outlet of said second gas container and said inlet of said flow meter, an imaging device; and a processor, said processor being positioned in operative communication with said flow meter, said flow control valve, said first and second pressure valves, and said imaging device, wherein said processor is configured to receive said first and second flow signals, wherein said processor is configured to selectively open said flow control valve in response to said first and second flow signals, and wherein said processor is configured to selectively activate said imaging device in response to said first and second flow signals.

2. The system of claim 1, wherein said processor is configured to determine a monitored flow ratio corresponding to the ratio between the oxygen gas and the gaseous contrast agent within the flow meter, and wherein the processor is configured to compare the monitored flow ratio to a desired flow ratio.

3. The system of claim 1, wherein said processor is configured to selectively open said first pressure valve such that a selected volume of said gaseous contrast agent enters said inlet of said flow meter, and wherein said processor is configured to selectively open said second pressure valve such that a selected volume of said oxygen gas enters said inlet of said flow meter.

4. The system of claim 3, wherein said subject has a respiratory cycle, wherein said processor is configured to open said first pressure valve, said second pressure valve, and said flow control valve such that delivery of said mixture of said gaseous contrast agent and said oxygen gas to said delivery tube is synchronized with a selected point in the respiratory cycle of said subject.

5. The system of claim 4, wherein said processor is configured to synchronize activation of said imaging device with the selected point in the respiratory cycle of said subject.

6. The system of claim 3, wherein the total volume of said selected volumes of said gaseous contrast agent and said oxygen gas substantially corresponds to a tidal volume of the lungs of the subject.

7. The system of claim 1, wherein said flow meter comprises a pneumotachometer.

8. The system of claim 1, wherein said imaging device comprises a magnetic resonance imaging (MRI) machine.

9. The system of claim 1, further comprising an interface element coupled to said second end of said delivery tube and configured for operative coupling to the mouth of the subject.

10. The system of claim 9, wherein said interface element comprises a facemask.

11. The system of claim 9, wherein said interface element comprises a mouthpiece.

12. The system of claim 1, further comprising a collection container defining an interior space and having an inlet in fluid communication with said first end of said delivery tube, said collection container being configured to receive expired gases from said subject.

13. The system of claim 12, further comprising a second flow control valve positioned between said first end of said delivery tube and said inlet of said collection container, said second flow control valve being positioned in fluid communication with said first end of said delivery tube and said inlet of said collection container, said flow control valve being configured to provide selective fluid communication between said delivery tube and said inlet of said collection container.

14. The system of claim 13, wherein said processor is in operative communication with said second flow control valve, wherein said processor is configured to selectively open said second flow control valve, and wherein said processor is configured to synchronize opening of said second flow control valve with expiration by said subject.

15. The system of claim 1, wherein said first gas container comprises a first reservoir bag, said first reservoir bag defining said outlet and said interior volume of said first gas container, and wherein said second gas container comprises a second reservoir bag, said second reservoir bag defining said outlet and said interior volume of said second gas container.

16. The system of claim 15, wherein said first gas container further comprises a first chamber, wherein said second gas container further comprises a second chamber, said first chamber being configured to receive at least a portion of said first reservoir bag, said second chamber being configured to receive at least a portion of said second reservoir bag, said first and second chambers defining respective openings, wherein at least a portion of said outlet of said first reservoir bag is received within said opening of said first chamber, and wherein at least a portion of said outlet of said second reservoir bag is received within said opening of said second chamber.

17. The system of claim 16, wherein the first and second chambers are configured to receive an inert gas, and wherein the processor is configured to selectively adjust the pressure within each respective chamber.

* * * * *